United States Patent [19]

Sugg et al.

[11] Patent Number: 5,380,872
[45] Date of Patent: Jan. 10, 1995

[54] MODULATORS OF CHOLECYSTOKININ

[75] Inventors: Elizabeth E. Sugg, Durham; Milana Dezube, Chapel Hill; Gavin C. Hirst, Carrboro, all of N.C.

[73] Assignee: Glaxo Inc., Research Triangle Park, N.C.

[21] Appl. No.: 914,918

[22] Filed: Jul. 14, 1992

[51] Int. Cl.$^6$ .......................................... C07D 209/20
[52] U.S. Cl. ................................. 548/495; 548/496
[58] Field of Search ................ 548/495, 496; 514/419

[56] References Cited

U.S. PATENT DOCUMENTS

| 4,490,364 | 12/1984 | Rivier | 424/177 |
| 4,624,962 | 11/1980 | Henning et al. | 548/495 |

FOREIGN PATENT DOCUMENTS

| 268297A2 | 11/1987 | European Pat. Off. |
| 381340A2 | 1/1990 | European Pat. Off. |
| 405537A1 | 6/1990 | European Pat. Off. |
| WO90/06937 | 6/1990 | WIPO |
| WO91/19733 | 12/1991 | WIPO |
| WO92/04025 | 3/1992 | WIPO |
| WO92/04038 | 3/1992 | WIPO |
| WO92/04045 | 3/1992 | WIPO |
| WO92/04320 | 3/1992 | WIPO |
| WO92/04322 | 3/1992 | WIPO |
| WO92/04348 | 3/1992 | WIPO |

OTHER PUBLICATIONS

Horwell, et al. *J. Med. Chem.* 1991, 34, 404–401 "Rationally Designed 'Dipeptoid' Analogues of CCK. α-Methyltryptophan Derivatives as Highly Selective and Orally Active Gastrin and CCK-B antagonists with Potent Anxiolytic Properties".

Jensen, et al. *Biochem. Biophys. Acta.* 1983, 757, 250–258 "COOH-Terminal Fragments of Cholecystokinin-A New Class of Cholecystokinin Receptor Antagonists".

Spanarke., et al. *J. Bio. Chem.* 1983, v. 258, 11, 6746–6749 "Cholecystokinin-27-32-Amide".

Shiosake, et al. *J. Med. Chem.* 1990, 33, 2950–2952 "Development of CCK-Tetrapeptide Analogues as Potent and Selective CCK-A Receptor Agonists".

Drysdale, et al. *J. Med. Chem.* 1992, 35, 2573–2581 "Rationally Designed 'Dipeptoid' Analogues of CCK. Acid Mimics of the Potent and Selective Non-Peptide CCK-B Receptor Antagonist Cl-988".

*Primary Examiner*—David B. Springer
*Attorney, Agent, or Firm*—R. Cole Harrington; David J. Levy

[57] ABSTRACT

CCK modulators, e.g. agonists or antagonists, of the following formula (I):

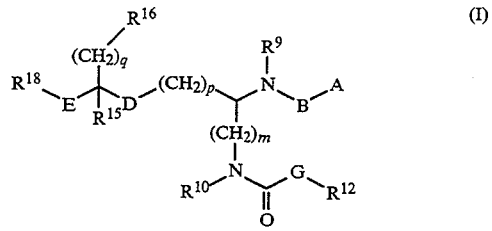

or a base-addtion salt thereof.

6 Claims, No Drawings

MODULATORS OF CHOLECYSTOKININ

FIELD OF THE INVENTION

The invention relates to chemical compounds which modulate the hormone cholecystokinin (CCK) in mammals. Effects of such modulation include the regulation of appetite, and treatment of gastrointestinal disorders (including gallbladder disorders), central nervous system disorders and pain.

BACKGROUND OF THE INVENTION

CCK is a gastrointestinal hormone of 33 amino acids which is utilized by the body in the cascade of events which are part of hunger, eating, digestion and satiety. Other such hormones include gastrin and secretin. The presence of acid, fat and protein breakdown products or any irritating factor in the upper small intestine causes the release of secretin and CCK. Both of these are important for control of pancreatic secretion and CCK is essential for emptying of the gallbladder, see Chapter 64, entitled "Secretory Functions of the Alimentary Tract" in *A.C. Guyton's Textbook of Medical Physiology*, W. B. Saunders, 1986 Philadelphia.

CCK has a variety of regulatory roles in the periphery including gallbladder contraction and pancreatic enzyme secretion (V. Mutt in "Gastrointestinal Hormones", G. B. J. Glass, ed, Raven Press, New York, 1980 pp. 169; J. A. Williams, *Biomed. Res.*, 1982 pp. 3:107), inhibition of gastric emptying and suppression of food intake. CCK and its fragments are believed to play an important role in appetite regulation and satiety (Della-Fera, *Science*, 1979 pp. 206:471; Saito et al., *Nature*, 1981 pp. 289:599; and Smith "Eating and its Disorders", A. J. Stunkard and E. Stellar, eds., Raven Press, New York, 1984 p. 67) and recently, patients with bulimia were shown to have lower than normal CCK levels in their plasma (Geracioti et al., *New England Journal of Medicine*, 1988 pp. 319:683).

CCK in the brain has been suggested to have a role in schizophrenia (N. P. V. Nair et al, *Prog. Brain Res*, 1986 pp. 65:237), memory and cognition (S. Itoh and H. Lal, *Drug Dev. Res.*, 1990, pp. 21:257), and CCK antagonists have been suggested to be potentially useful in drug abuse therapy (B. Costall et al. in "Proceedings of the Cambridge Symposia, The Neurological Basis of Anxiety," Robinson College, Cambridge, U.K., Sep. 7 and 8, 1990).

Two sub-types of the CCK receptor have been identified. Type-A CCK receptors, commonly referred to as the "peripheral-type" receptor, are primarily found in the pancreas, gallbladder, ileum, pyloric sphincter and on vagal afferent nerve fibers. Type-A CCK receptors bind CCK-8 with high affinity but have low affinity for desulfated CCK-8 and CCK-4. The brain contains predominantly the Type-B receptors that bind CCK-8, desulfated CCK-8 and CCK-4 with high affinity. Type-A CCK receptors are found in the brain, although in low abundance (D. R. Hill et al., *Brain Res*, 1988, pp. 454:101-5; D. R. Hill et al., *Neurosci Lett.*, 1988, pp 89:133-9; R. W. Barrett et al., *Mol. Pharmacol*, 1989, 36:285-90; and D. R., Hill et al., *J. Neurosci*, 1990, 10:1070, 81), and play an important role there also (V. Dauge et al., *Pharmacol Biochem Behav.*, 1989 33:637-40). Type-A receptor-selective CCK agonists are currently of particular interest as potential anorectic agents because of the ability of CCK-8 and Type-A CCK-selective agonists to suppress food intake in several animal species (Della-Fera et al., *Science*, 1979, 206:471; K. E. Asin et al., *Intl Conference on Obesity.*, 1990, Abstract p. 40).

Obesity is a major disorder affecting as much as one third of the North American population. Several studies have shown that such individuals are at increased risk in developing cardiovascular disease (hypertension and hypercholesterolemia), diabetes and several types of cancer. The effective treatment of obesity, however, remains a largely unachieved goal. Existing pharmacotherapeutic approaches to weight loss involve the use of amphetamine-based agents such as amphetamine, diethylpropion, mazindol and fenfluramine which act directly on the CNS to lower food intake by modulating dopaminergic, adrenergic and/or serotonergic mechanisms. Although weight loss can be achieved with such agents, their use is restricted due to CNS side-effects, potential addiction liability and the production of tolerance to their actions, with chronic administration leading to potential depression, vestibular disturbances, hallucinations and addiction, as well as interference with the actions other drugs such as MAO inhibitors and antihypertensives. There is also a subpopulation of obese patients that is refractory to present anorectic drug treatments.

Additional roles for CCK in the periphery (body) include stimulation of gall bladder contraction, and inhibition of gastric emptying. CCK in the brain has been suggested to have a role in schizophrenia, memory and cognition and CCK antagonists have been suggested to be useful in drug abuse therapy, all as set forth in the previous citations or in citations therein.

CCK agonists or analogs of CCK-8, a particular biologically active form of CCK, have been published. For example, U.S. Pat. No. 4,490,364, issued Dec. 25, 1984 discloses heptapeptide, octapeptide and nonapeptide analogs of CCK-8 as CCK agonists for stimulating gallbladder contractions, arresting the secretion of gastric acid and treating convulsions.

European Patent Application EP381,340, published Aug. 8, 1990, and European Patent Application EP 268,297, published May 25, 1988, disclose hepta- and octapeptides with sulfate ester groups which are useful for treating obesity.

Orally active CCK-B receptor selective dipeptoid antagonists are described in European Patent 465,537 published Jan. 2, 1991 and by D. C. Horwell et al., in *J. Med. Chem.*, 34, 1991, pp. 404–414. These compounds have weak CCK-A receptor affinity, being >500-fold selective for CCK-B receptors, and are reported to be useful as anti-anxiety and anti-ulcer agents. These compounds also possess weak anorectic activity resulting from their weak affinity for CCK-A receptors. Six related disclosures have been published. PCT WO 92/04348 published March 19, 1992 teaches carboline derivatives useful in treating obesity while cholecystokinin antagonists are described in PCT WO 92/04045 and WO 92/04025. Dipeptoids to treat obesity are taught in PCT WO 92/04322 while pro-drugs to dipeptoids are shown in PCT WO 92/04038. Peptoids for treating obesity are found in PCT WO 92/04320.

CCK antagonists or gastrin receptor antagonists comprising C-terminal fragments of CCK have recently been reported. See Jensen et al., *Biochem. Biophys. Acta*, 1983, pp. 757-250; Spanarkel, *J. Biol. Chem.* 1983, pp. 258-6746. Japanese Patent Application 45/1050 to Miyao et al. discloses a tetrapeptide derivative of the carboxy terminal sequence of gastrin (L-Trp-L-Lys-L-Asp-L-PheNH$_2$) which acts as antagonists of gastrin.

CCK-A receptor selective tetrapeptide agonists are described in the literature as agents to treat gastrointestinal disorders (including gall bladder stasis), CNS disorders and pain as well as appetite regulation, see PCT WO 91/19733 published Dec. 26, 1991, by K. Shiosaki et al., in *J. Med. Chem.*, 33, 1990 pp. 2950–2952 and in PCT WO 90/06937, published Jun. 28, 1990.

The present invention describes CCK-A receptor selective agents which modulate peripheral CCK receptors.

SUMMARY OF THE INVENTION

Cholecystokinin receptor ligands of the formula (I):

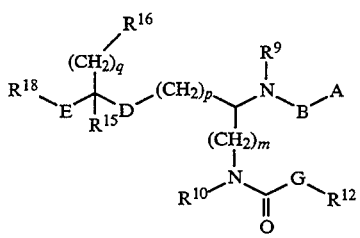

or a pharmaceutically acceptable salt thereof, wherein A, B, D, E and G and m, q, and $R^{12}$, $R^{15}$, $R^{16}$, and $R^{18}$ are defined herein, are useful as modulators of CCK with specific utilities including the induction of weight loss. Also claimed are pharmaceutical compositions of these compounds and methods for their use as pharmaceuticals, intermediates in their synthesis as well as the synthesis itself.

DETAILED DESCRIPTION OF THE INVENTION

Compounds of formula (I) above are part of the invention where:
A is selected from
 —COOR$^1$,
 —CONHR$^1$,
 —CN,
 —CHN$_4$, i.e. C-linked tetrazole,
 —CONHSO$_2$R$^2$,
 —CH$_2$OR$^1$,
 —CH$_2$SR$^1$,
 —P—O(OR$^1$)$_2$,
 —CO—NHOH,

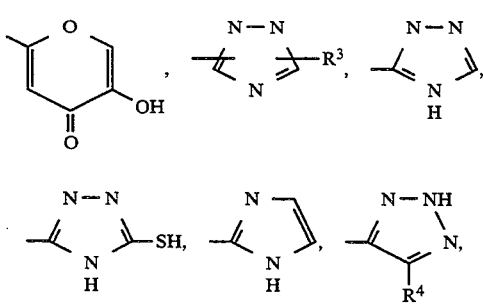

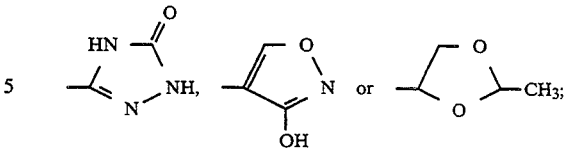

$R^1$ is H or lower alkyl;
$R^2$ is lower alkyl, fluoro lower alkyl, aryl, substituted aryl or OH;
$R^3$ is OH, NH$_2$ or CH$_3$;
$R^4$ is CN, CO$_2$H or CF$_3$;
B is selected from
 i) —COCH(NHR$^5$)—(CH$_2$)$_n$—;
 ii) —COCH$_2$(CH$_2$)$_n$—;
 iii) —CO—CH=CH—, cis or trans;
 iv) —CO—phenylene—, ortho, meta or para;
 v) —CH$_2$—(CH$_2$)$_n$—;
 vi) —CH(COOR$^6$)—CH$_2$—(CH$_2$)$_n$—;
where
n is 0, 1 or 2;
$R^5$ is H, lower alkyl, COR$^7$ or CONHR$^8$;
$R^6$ is H, lower alkyl, aryl, substituted aryl or arylalkyl;
$R^7$ is H, lower alkyl, aryl, substituted aryl or arylalkyl;
$R^8$ is H, lower alkyl, aryl, substituted aryl or arylalkyl;
$R^9$ is H or lower alkyl;
$R^{10}$ is H or lower alkyl;
m is 1, 2, 3 or 4;
G is —O—, —CH$_2$—, —NR$^{11}$—, —CH=CH—, cis or trans;
$R^{11}$ is H or lower alkyl;
$R^{12}$ is selected from
 i) alkyl;
 ii) alkenyl;
 iii) cyclo (C$_3$–C$_{10}$ alkyl);
 iv) heterocyclic;
 v) substituted heterocyclic;
 vi) arylalkyl;
 v) aryl, having 1 or 2 substituents independently selected from the group consisting of:
  a) hydroxyl,
  b) halogen,
  C) —OSO$_3$R$^{13}$,
  d) nitro,
  e) cyano,
  f) amino,
  g) lower alkylamino,
  h) (lower alkyl)$_2$ amino,
  i) lower alkyl,
  j) halo lower alkyl,
  k) lower alkoxy,
  l) C$_2$–C$_4$-alkanoyl,
  m) lower alkoxy carbonyl, and
  n) phenoxy
$R^{13}$ is H or lower alkyl;
p is 0, 1, 2;
D is
 i) —NH—CO—,
 ii) —CO—NR$^{14}$—,
 iii) —(CH$_2$)$_r$—NR$^{14}$—,
 V) —NR$^{14}$—(CH$_2$)$_r$—
r is 0, 1 or 2
$R^{14}$ is H or lower alkyl;
$R^{15}$ is H or lower alkyl;
q is 0 or 1;
$R^{16}$ is selected from
 i) aryl or substituted aryl, ii) substituted aryl,
iii) heteroaryl,
iv) substituted heteroaryl, or
v) bicyclic heteroaryl;

E is selected from
i) —NH—CO—,
ii) —CO—NR$^{17}$—,
iii) —NH—CO—NR$^{17}$—,
iv) —O—CO—NR$^{17}$—,
v) —SO$_2$—NR$^{17}$—, or
vi) —(CH$_2$)$_r$—NR$^{17}$—;

R$^{17}$ is H or lower alkyl,
R$^{18}$ is selected from
i) C$_1$-C$_{10}$ alkyl or C$_2$-C$_{10}$ alkenyl,
ii) C$_3$-C$_{10}$ mono, bi- or tri-cycloalkyl with zero to four substituents independently selected from the group consisting of
a) alkyl,
b) halogen,
c) CN,
d) —OR$^{19}$,
e) —SR$^{19}$,
f) —CO$_2$R$^{19}$,
g) —CF$_3$,
h) —NR$^{19}$R$^{20}$,
i) —(CH$_2$)$_s$ OR$^{19}$, and
j) —(CH$_2$)$_s$ COOR$^{19}$;
iii) heterocyclic,
iv) substituted heteroaryl,
v) arylalkyl,
vi) aryl,
vii) aryl having 1 or 2 substituents independently selected from s is an integer from 0 to 6;
R$^{19}$ is H or lower alkyl; and
R$^{20}$ is H or lower alkyl.

The pharmaceutically acceptable salts of the acids of formula (I) are readily prepared by conventional procedures such as treating an acid of formula (I) with an appropriate amount of a base, such as an alkali or alkaline earth metal hydroxide e.g. sodium, potassium, lithium, calcium, or magnesium, or an organic base such as an amine, e.g., dibenzylethylenediamine, cyclohexylamine, dicyclohexylamine, trimethylamine, piperidine, pyrrolidine, benzylamine and the like, or a quaternary ammonium hydroxide such as tetramethylammonium hydroxide and the like.

In the definitions for the above formula (I), lower alkyl may be of 1–6 carbons, straight or branched chain; alkyl may be of about 1–10 carbons, straight or branched chain such as but not limited to methyl, ethyl, n-propyl, iso-butyl or 3-methyl pentyl; alkenyl may be from about 2 to 6 carbons; halogen may be fluoro, chloro, bromo or iodo; the definitions for divalent moieties such as B, D, E and G are read exactly as shown above into formula (I) e.g. if B is —COCH$_2$(CH$_2$)—, the —CO— portion is attached to the NH of (I) while the —(CH$_2$)— is attached to the A moiety.

Particular compounds of Formula (I) are those of the following formulae (Ia), (Ib), (Ic), (Id) and (Ie), and wherein * is R or S and ** is R or S and preferably * is R and ** is R or S:

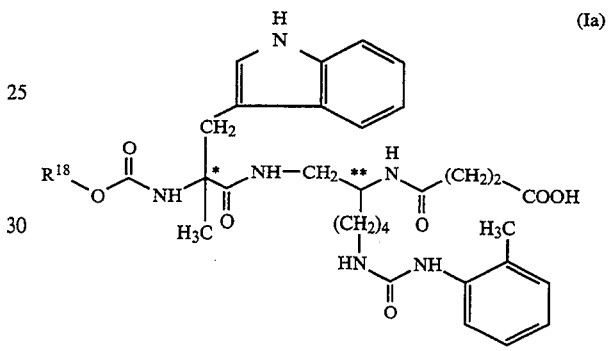

(Ia)

where R$^{18}$ is benzyl, adamantyl, t-butyl or trans-2-methylcyclohexyl; and

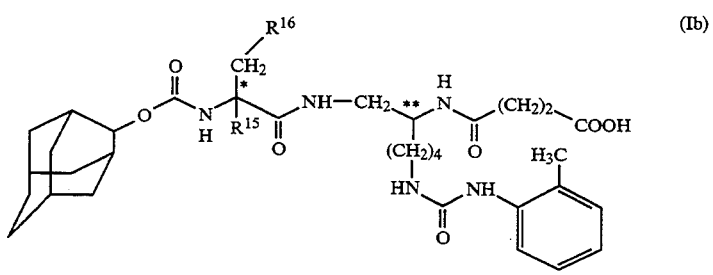

(Ib)

where R$^{15}$ is methyl and R$^{16}$ is 3-quinolyl, 2-naphthyl, 3-indolyl, 2-indolyl or phenyl; or R$^{15}$ is hydrogen and R$^{16}$ is 3-indazolyl, 3-quinolyl, 2-naphyl, 3-indolyl, 2-indolyl or phenyl; and

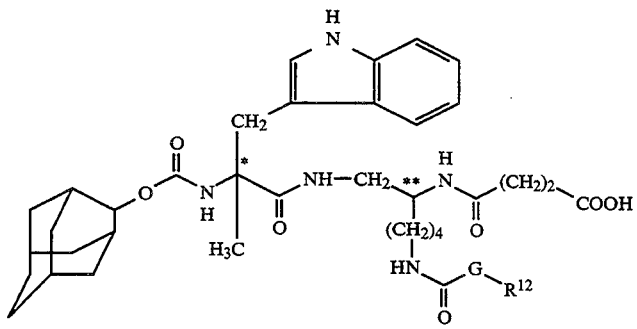

(Ic)

where G is —O— or —NH— and $R^{12}$ is phenyl, 2-methylphenyl, 2-chlorophenyl, 2-methoxyphenyl or 2-nitrophenyl; or G is —CH=CH— and $R^{12}$ is phenyl, 4-methylphenyl, 4-chlorophenyl, 4-methoxyphenyl, 4-hydroxyphenyl or 4-nitrophenyl; or G is —CH$_2$— or —CH$_2$CH$_2$— and $R^{12}$ is any of the values given above for $R^{12}$ Formula (I); and

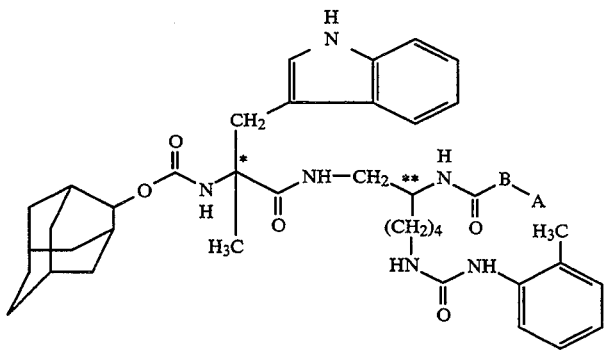

(Id)

wherein B is $(CH_2)_n$, n=1, 2, 3, CH=CH, cis or trans and A is $CO_2H$, $CO_2CH_3$, $CHN_4$, $NHSO_2CF_3$ or $NHSO_2CH_3$; and

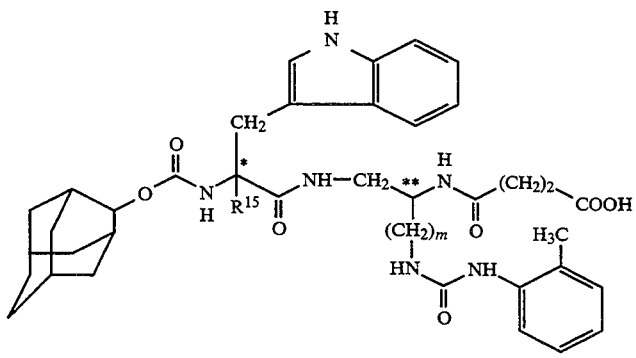

(Ie)

Preferred for agonist activity is $R^{15}$=CH$_3$; m=3, 4; and ** is R or S.

Preferred for antagonist activity is $R^{15}$=H; m=1-4; * is R; ** is R or S.

Compounds of formula (I) are CCK-A modulators, e.g. antagonists or agonists, and would be useful in the treatment and prevention of CCK-related disorders of the gastrointestinal and appetite systems of animals, especially man. CCK-A agonists would be useful in the treatment of obesity or gall bladder disorders e.g. gall stones, while CCK-A antagonists would be useful in the treatment of pancreatic cancer, and as central nervous system suppressants, e.g. anti-psychoties.

The present invention is also directed to pharmaceutical compositions comprising a therapeutically-effective amount of the compound of formula (I) and a pharmaceutically-acceptable carrier or diluent, as well as to a method of treating gastrointestinal disorders (including gallbladder disorders), CNS disorders, insulin-related disorders and pain, or of regulating appetite in humans and lower mammals, by administration of a compound of formula (I).

Preferred embodiments of this invention are when $R^{18}$ is a substituted or unsubstituted $C_6$ to $C_{10}$ cycloalkyl or polycycycloalkyl of the following formulae (i)-(iv):

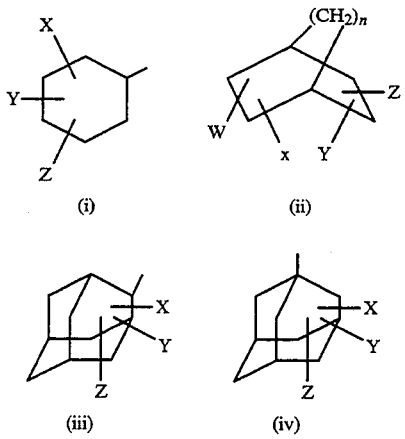

wherein W, X, Y, and Z are independently H, $C_1$–$C_6$ straight or branched alkyl, $CF_3$, $NR^{19}R^{20}$, $(-CH_2)_s$ $COOR^{19}$, CN, F, Br, Cl, $OR^{19}$ or $SR^{19}$.

Preferred compounds for CCK-A antagonists are $R^{15}$=H, m=1, 2, 3, 4.

Preferred compounds for CCK-A agonist activity are $R^{15}$=$CH_3$, m=3, 4.

Also preferred is when $R^{16}$ is indole, napthyl or quinoyl. Also preferred is when p=1, E=OCONH and D=CONH.

Particular subgroups of formula (I) are those wherein:

i) —B—A is —CO—$CH_2CH_2COOH$; —$COCH_2(CH_2)_n$—$NHSO_2CF_3$ where n is 0 or 1; or ii) —G—$R^{12}$ is —NH phenyl with Cl, $OCH_3$ or $CH_3$ substitution at the ortho position; and/or iii) $R^{18}$ is adamantane, norbornane, 2-methylcyclohexyl or tert-butyl.

The compounds of the present invention can have multiple chiral centers, depending on their structures, and may exist as diastereomers, mixtures of diastereomers, or as a mixture of the individual enantiomers. The present invention contemplates all such forms of the compounds. The mixtures of diastereomers are typically obtained as a result of the reactions described more fully below. Individual diastereomers may be separated from mixtures by conventional techniques such as column chromatography or repetitive recrystallizations. Individual enantiomers may be separated by conventional methods such as conversion to a salt with an optically active compound followed by recrystallization. Alternatively, chiral chromatography may be used.

Individual a-amino acids are known, or if not known, may be synthesized and resolved by methods within the skill of the art.

Two key intermediates are essential to the present invention: triamino intermediate (II) and b-diamino acid (III):

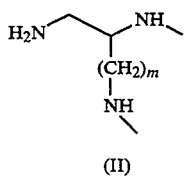

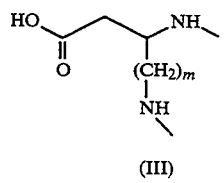

The intermediates (II) and (III) are derived from naturally occurring L- or D-a-amino acids (m=3, 4) or synthetic a-amino acids (m=1, 2). Where m=4, N-a-protected L or D lysine may be purchased. Where m=3, N-a-protected L- or D-ornithine may be purchased. Where m=1, 2, compounds are obtained by the following route illustrated in Scheme 1 for L- or D-asparagine, or L- or D-glutamine, respectively, using the method of Waki, et al (Synthesis (1981) 266–268).

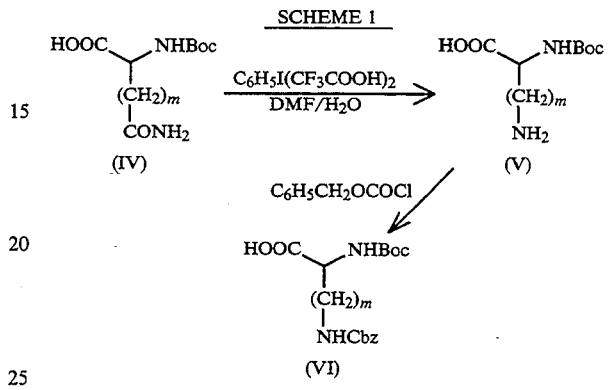

wherein BOC is t-butyloxycarbonyl.

Scheme 1 above describes the synthesis of differentially protected amino acids of formula VI, which involves treating N-a-t-butyloxycarbonyl-asparagine or glutamine with iodobenzenetrifluoroacetate in aqueous N,N-dimethylformamide to effect the Hofmann reaction. The free amine, compound V, is then suitably protected with benzyl chloroformate and triethylamine to give the carbobenzyloxycarbamate. N-a-t-butyloxycarbonyl-ornithine or lysine can be similarly protected, at the d-NH or e-NH, respectively.

The synthesis of a suitably protected triamino intermediate (II) is illustrated in Scheme 2:

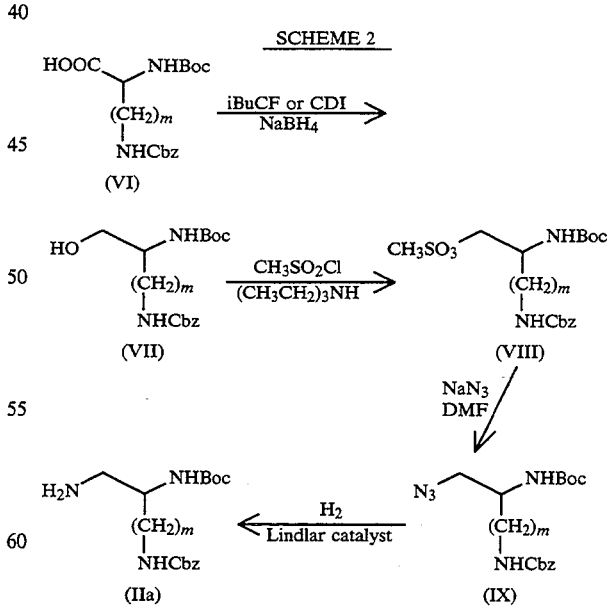

Scheme 2 above illustrates procedures for preparing intermediates useful in producing final products of Scheme 6.

Key intermediate IIa is prepared by first reducing the carboxylic acid of compound VI to an alcohol. In one process the acid is activated with isobutylchloroformate (iBuCF) and Hunig's base in a solvent such as THF at about 0° C. In another process the acid is treated with carbonyl diimidazole (CDI) in THF at room temperature. The activated ester or imidazolide is then reduced to an alcohol with a reducing reagent such as sodium borohydride or lithium aluminum hydride. The alcohol, dissolved in dichloromethane, is treated with methanesulfonyl chloride and triethylamine to give the corresponding mesylate. The mesylate is treated with sodium azide in N,N-dimethylformamide (DMF) to produce the azide. The azide is hydrogenated over a Lindlar catalyst to form amine IIa.

Alternatively, the side chain nitrogen may be functionalized prior to the synthesis of the triamino intermediate. This synthesis is illustrated in Scheme 3, where J=NH, CH$_2$, particular values of G, N-a-t-butyloxycarbonyl (as illustrated), or the N-a-benzyloxycarbonyl protecting groups may be used.

room temperature. The carboxylic acid is activated with such reagents as isobutylchloroformate (iBuCF) and Hunig's base or carbonyl diimidazole (CDI) in THF and the ester or imidazolide is reduced to an alcohol with reagents such as sodium borohydride or lithium aluminum hydride.

The alcohol, dissolved in dichloromethane, is treated with methanesulfonyl chloride and triethylamine to give the corresponding mesylate. The mesylate is treated with sodium azide in N,N-dimethylformamide to produce the corresponding azide. The azide is hydrogenated in the presence of a catalyst such as ten percent palladium on carbon to form amine (IIIb).

The synthesis of a suitable protected b-diamino acid intermediate (III) is illustrated in Scheme 4.

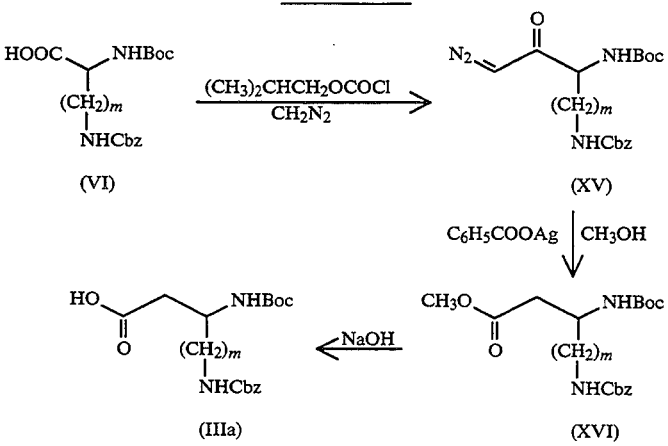

Scheme 4 above illustrates procedures for preparing intermediates useful in producing final products of Scheme 7.

In one process differentially protected N-a-t-butyloxycarbonyl-N-e-carbobenzyloxylysine is homologated using the Arndt Eistert reaction. The acid is treated

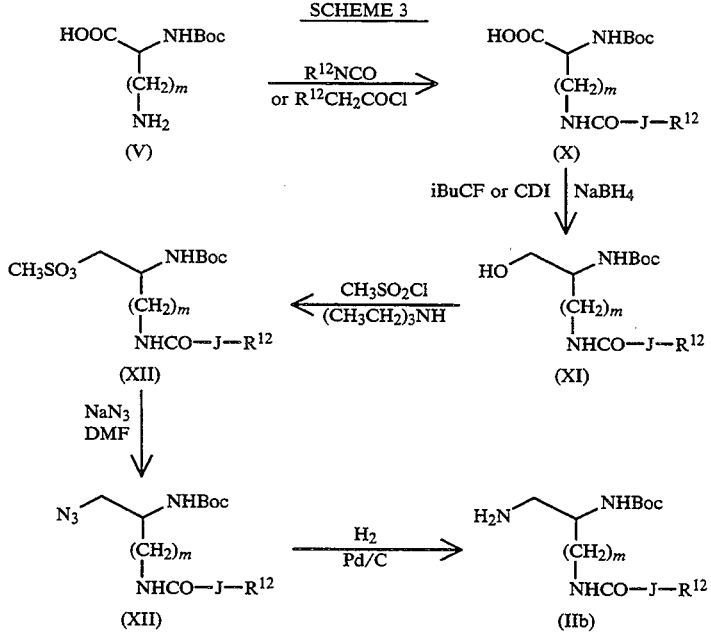

Scheme 3 above illustrates procedures for preparing intermediates useful in producing final products.

One process involves treating N-a-t-butyloxycarbonyl-lysine with isocyanates in 1N sodium hydroxide at with isobutylchloroformate (iBuCF) and triethylamine in a solvent such as THF followed by addition of diazomethane to give the corresponding diazomethylketone. A methanol solution of the diazomethylketone is treated with silver benzoate to obtain the homologated methyl ester. This then is treated with lithium hydroxide and stirred at room temperature overnight to produce the corresponding carboxylic acid.

Alternatively, the side chain may be functionalized prior to synthesis of intermediate (III), as illustrated in Scheme 5, where J=NH, CH$_2$, particular values of G.

SCHEME 6

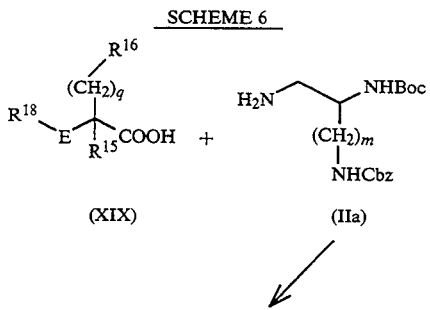

SCHEME 5

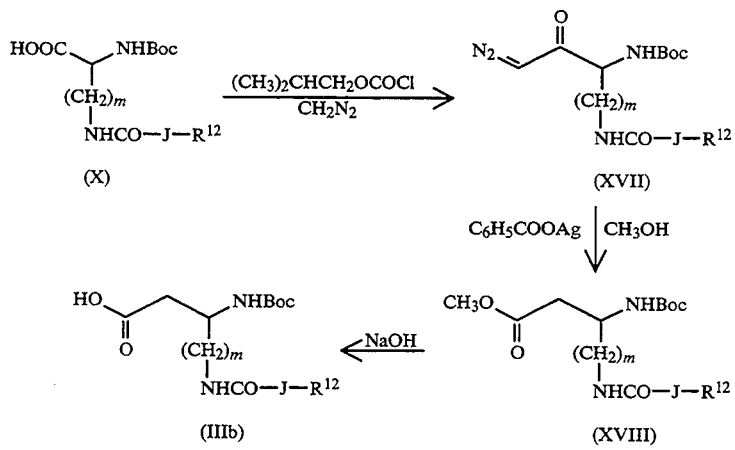

Scheme 5 above illustrates procedures for preparing intermediates useful in producing final products.

In one process N-a-t-butyloxycarbonyl-N-e-o-tolylaminocarbonyl-lysine is homologated using the Arndt Eistert reaction. The acid is treated with isobutylchloroformate (iBuCF) and triethylamine in a solvent such as THF followed by addition of diazomethane to give the corresponding diazomethylketone. A methanol solution of the diazomethylketone is treated with silver benzoate to obtain the homologated methyl ester. This then is treated with lithium hydroxide and stirred at room temperature overnight to produce the corresponding carboxylic acid.

Intermediates (IIa) and (IIIa) can be used to build the molecules, allowing flexible introduction of side chain substituents. Protected L- or D-amino acids can be coupled to intermediate IIa and L- or D-amino acid amides can be coupled to intermediate IIIa, utilizing known literature methods. Suitable coupling agents include dicyclohexyl carbodiimide (DCC), 1-(3-dimethylaminopropyl)-3-ethyl carbodiimide hydrochloride (EDC), or bis(2-oxo-3-oxazolidinyl) phosphinic chloride. N-Hydroxybenzotriazole (HOBt) or N-hydroxy succinimide (NHS) may be added to improve coupling rates and inhibit racemization. Suitable solvents include dichloromethane (DCM) and dimethylformamide (DMF). An example of such coupling is shown in the following Schemes 6 and 7.

![Structure XX]

Where E, R$^{15}$, R$^{16}$ and R$^{18}$ are as previously defined.

In one process a solution of 2-adamantyloxycarbonyl-α-methyl-D,L-tryptophan in dichloromethane reacts with an equimolar solution of 1-hydroxybenztriazole, key intermediate (IIa), and 1-(3-dimethylaminopropyl)-3-ethylcarbodiimide hydrochloride. The reaction mixture is allowed to react at room temperature overnight to form the carbobenzyloxy-protected product (XX).

SCHEME 7

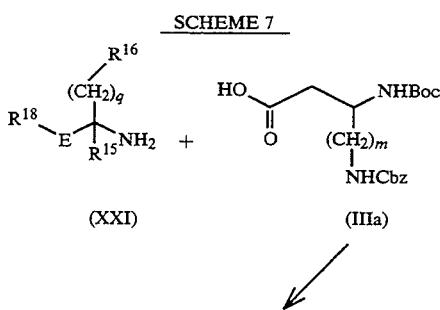

-continued
SCHEME 7

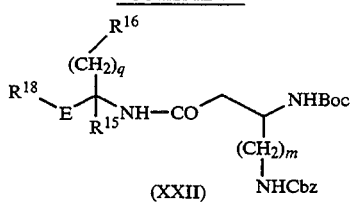

(XXII)

Where E, $R^{15}$, $R^{16}$ and $R^{18}$ are as previously defined.

In Scheme 7 a solution of 2-adamantyloxycarbonyl-a-methyl-(D,L)-tryptophan in dichloromethane reacts with an equimolar solution of 1-hydroxybenztriazole, key intermediate IIIa, and 1-(3-dimethylaminopropyl)-3-ethylcarbodiimide hydrochloride. The reaction mixture is allowed to react at room temperature overnight to form the carbobenzyloxy protected product (XXII).

Intermediates (XX) and (XXII) may be deprotected using acid, such as HCl or TFA, and the C-terminal group introduced either by reaction with anhydrides, amino acid active esters, or by coupling with appropriate amino acid esters, diacid half esters, or other suitable derivatives consistent within the compounds of the invention as shown in the following Scheme 8 wherein (XXIII) is an intermediate within Formula (XX) or (XXII):

SCHEME 8

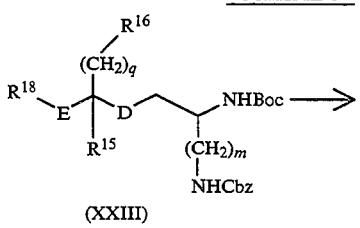

(XXIII)

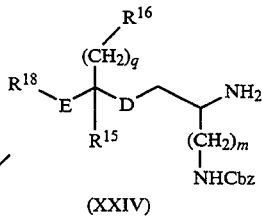

(XXIV)

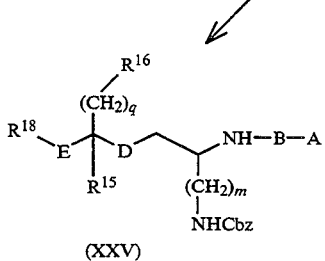

(XXV)

In one procedure compound (XXIII) was treated with 4N hydrochloric acid in dioxane to obtain the hydrochloride salt of (XXIV). This then is dissolved in dichloromethane with triethylamine and reacted with succinic anhydride to form the succinyl free acid.

Intermediate (XXV) may be deprotected using $H_2$ and a suitable catalyst; or HBr/HOAc to give (XXVI) which may be heated with isocyanates, acid halides, carbamoyl halides, cinnamoyl halides, alcohols with CDI, to give compounds of Formula (I) according to Scheme 9:

SCHEME 9

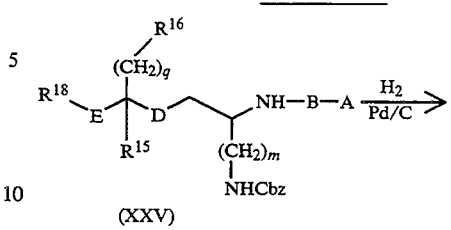

(XXV)

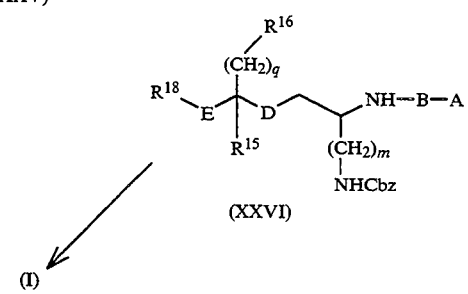

(XXVI)

(I)

In another process compound (XXV) was hydrogenated in the presence of a catalyst such as ten percent palladium on carbon to form the amine XXVI. Alternatively, where the side chain functionality is defined, intermediates (IIb) and (IIIb) may be reacted in the same synthetic schemes to give a compound of Formula (XXVII):

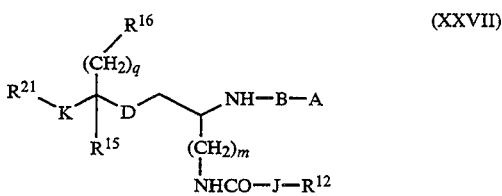

(XXVII)

where K is oxycarbonylamino or oxycarbonyl and $R^{21}$ is fluorenyl or benzyl, or $C_1$-$C_2$ alkyl.

After deprotection of the ester or amine, intermediates (XXVII) and (XXIX) can be used to prepare compounds of claim (I) through reaction of (XXVIII).

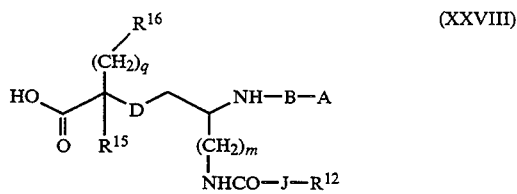

(XXVIII)

with an appropriate amine in the presence of a dehydrating agent such as DCC, EDC or BOP; or the reaction of formula (XXIX):

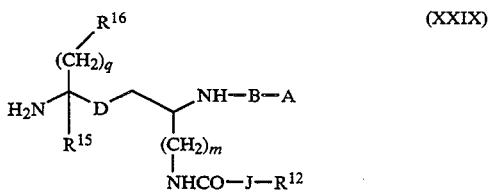

(XXIX)

with carbamoyl chlorides, alcohol with CDI, acid chlorides, acid anhydrides, protected amino acids, anhydrides, isocyanates.

When a compound of formula (I) is used as an agonist of CCK in a human subject, the total daily dose administered in single or divided doses may be in amounts, for example, from 0.001 to 1000 mg a day and more usually 1 to 1000 mg. Dosage unit compositions may contain such amounts of submultiples thereof to make up the daily dose.

The amount of active ingredient that may be combined with the carrier materials to produce a single dosage form will vary depending upon the host treated, the particular treatment and the particular mode of administration.

It will be understood, however, that the specific dose level for any particular patient will depend upon a variety of factors including the activity of the specific compound employed, the age, body weight, general health, sex, diet, time of administration, rate of execretion, drug combination and the severity of the particular disease undergoing therapy.

The compounds of the present invention may be administered sublingually, orally, parenterally, by inhalation spray, rectally or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsion, solutions, suspensions, syrups and elixirs containing inert diluents commonly used in the art, such as water. Such compositions may also comprise adjuvants, such as wetting agents, emulsifying and suspending agents and sweetening, flavoring and perfuming agents.

The present agents can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compostions in liposome form can contain, in addition to the tetrapeptide of the present invention, stabilizers, preservatives, excipients and the like. The preferred lipids are the phospholipids and the phosphatidyl cholines (lecithins) both natural and synthetic.

Methods to form liposomes are known in the art. See, for example, Prescott, Ed., Methods in Cell Biology, Volume XIV, Acedemic Press, New York, N.Y. (1976), p. 33 et seq.

CCK-A RECEPTOR BINDING ASSAY

Tissue Preparation:

Solutions of 0.3M Sucrose and 2.0M Sucrose are prepared and chilled overnight at 4° C. On the following day inhibitors are added such that the final concentrations are 0.01% Soybean Trypsin Inhibitor (50 mg/500 ml sucrose) and 100 mM Phenylmethlysulfonyl fluoride (8.5 mg/500 mL sucrose).

Rats are sacrificed by decapitation using a guillotine. The rat's external abdominal wall is wetted with methanol, and fur and skin are removed. The abdomen is opened, the pancreas is carefully dissected out, and placed in a 50 mL beaker containing 0.3M sucrose. After all the pancreata have been harvested, excess fat and lymph nodes are trimmed off. Pancreatic tissue is divided into approximately 4.0 g aliquots into 30 mL beakers, each containing 1.0 mL of 0.3M sucrose.

In 4° C. cold room, the pancreata are minced with scissors and diluted 1:10 weight:volume with 0.3M sucrose. Aliquots are homogenized in a chilled 40 mL Wheaton dounce with 4 up and down strokes of the "B" pestle followed by 4 up and down strokes of the "A" pestle. Homogenates are filtered through 2 layers of cheesecloth into a chilled 500 mL beaker, then diluted with 2.0M sucrose with stirring to yield a final concentration of 1.3M sucrose homogenate. This 1.3M homogenate is dispensed into 18 thin-walled 36 mL polyallomer tubes on ice (approximately 30 mL homogenate per tube), and each tube is overlaid with 0.3M sucrose until liquid is approximately 0.5 cm from the top of the tube. The samples are spun in a Sorvall RC70 ultracentrifuge at 27,500 RPM (100,000$\times$g) for 3 hours at 4° C. The interface band is collected into a chilled graduated cylinder, diluted and mixed with cold distilled water to a total volume of 312 mL, and spun at 100,000$\times$g for 50 min at 4° C. The pellets are resuspended in KRH buffers, transfered to a 15 mL Wheaton dounce, and homogenized with 4 up and down strokes of the matched "A" (tight) pestle. This homogenate is transferred into 2-27 mL polycarbonate bottles and spun at 100,000$\times$g for 30 min at 4° C. The pellet is resuspended (1 mL KRH buffer/gm wt of original tissue), transferred to an appropriate size dounce and homogenized with 4 up and down strokes of the matched "A" pestle. 1 mL aliquots are stored at −70° C. in microcentrifuge tubes.

| KRH Buffer: pH = 7.4 at 4° C. | | |
| --- | --- | --- |
| COMPONENT | MW | g/1 L |
| 25 mM HEPES | 260.3 | 6.51 |
| 104 mM NaCl | 58.44 | 6.08 |
| 5 mM KCl | 74.56 | 0.37 |
| 1 mM KPO$_4$ | 136.09 | 0.14 |
| 1.2 mM MgSO$_4$ | 246.48 | 0.30 |
| 2 mM CaCl$_2$ | 110.99 | 0.22 |
| 2.5 mM Glucose | 180.16 | 0.45 |
| 0.2% BSA | — | 2.00 |
| 0.1 mM PMSF* | 174.2 | 0.017 |
| 0.01% STI* | — | 0.10 |

*inhibitors added fresh the day of the experiment

Assay:

Test compounds are diluted in assay binding buffer in stock concentrations 10-fold more concentrated than desired final assay concentration.

50 mL test compound + 400 mL buffer + 25 uL [$^{125}$I]-sulphated CCK-8 labelled with Bolton and Hunter reagent (Amersham, 2000 Ci/mmol) + 25 mL prepared rat pancreas membranes are incubated for 30 minutes at 25° C. while shaking gently throughout the incubation.

1 mM L-364718 (final concentration) is used for determination of non-specific binding.

Reaction is stopped using Brandell Cell Harvester, washing 3× with 3 mL ice-cold (4° C.) assay binding buffer per wash.

Tissues are collected on Whatman GF/B filter papers pre-wet with assay buffer and filter papers are counted using a gamma counter.

CCK-B RECEPTOR BINDING ASSAY

Tissue Preparation:

Hartley Male Guinea Pigs (250–300 g, Charles River) are sacrificed by decapitation. The brain is removed and placed in 4° C. BUFFER (BUFFER = 50 mM Tris/HCL, pH = 7.4). The cortex is dissected and placed in 4° C. BUFFER. The total wet weight of all cortices is determined and the tissues are diluted 1:10 (wt:vol) with BUFFER.

The cortex is minced using a Tekmar Tissuemizer, then homogenized in BUFFER with 5 up/down strokes using a motor driven glass/teflon homogenizer. The preparation is maintained at 4° C. (on ice).

Membranes are pelleted by centrifugation in Sorvall RC5C at 4° C. using a SA600 rotor spun at 16,000 RPM (47,800×g Maximum). The pellet is saved and the supernatent is discarded. The pellets are combined and resuspended in buffer at 4° C. using same volume as above and blended, as above with 5 up/down strokes of a glass/teflon motor driven homogenizer using the same volume as before. The resulting homogenates are spun at 16,000 RPM (47,800×g Maximum, 36592×g Average) for 15 minutes at 4° C. Pellets are saved and the supernatents are discarded. Pellets are combined with BUFFER to get a final volume of 300 mL, and blended using a Tekmar Tissuemizer. Initial protein content is determined by the Biorad protein assay. The volume of suspension is adjusted with BUFFER, such that this volume adjustment yields approx. 4.0 mg/mL final concentration confirmed via Biorad protein assay. The final suspension is transferred as 4.0 mL aliquots into plastic tubes, and frozen at −70° C.

Assay:

BUFFER is 20 mM Hepes, 1 mM EGTA, 118 mM NaCl, 5 mM KCL, 5 mM MgCl$_2$, 0.05% BSA at pH = 7.4.

Skatron filters are soaked in BUFFER with 0.1% Bovine Serum Albumin (BSA) for an hour prior to harvesting.

100 mM Bestatin and 3 mM Phosphoramidon are prepared fresh. (Final assay concentrations will = 10 mM respectively.)

Test compounds are diluted in assay binding buffer in stock concentrations 10-fold more concentrated than desired final assay concentrations. [$^{125}$I]-sulfated CCK-8 labelled with Bolton-Hunter reagent (Amersham, 200 Ci/mmol) is diluted.

25 mL 100 mM Bestatin + 25 mL 3 mM Phosphoramidon + 25 mL test compound + 50 mL radioligand + 25 mL buffer + 100 mL guinea pig cortex membranes are incubated 150 minutes at room temperature.

For B$_o$ determination, assay binding buffer is substituted for test compound.

For filter binding determination, assay buffer is substituted for test compound and guinea pig cortex membranes as well.

For non-specific binding determination, 1 mM sulphated CCK-8 (Sigma) is substituted for test compound.

Reaction is stopped by filtering using the automated Skatron Cell Harvester. The filters are rinsed using 4° C. BUFFER. The filters are punched, placed in tubes and counted using a gamma counter.

GUINEA PIG GALL BLADDER ASSAY

Tissue Preparation:

Gall bladders are removed from guinea pigs sacrificed by cervical dislocation. The isolated gall bladders are cleaned of adherent connective tissue and cut into two rings from each animal (2–4 mm in length). Rings are suspended in organ chambers containing a physiological salt solution of the following composition (mM): NaCl (118.4); KCl (4.7); MgSO$_4$xH$_2$O (1.2);CaCl$_2$x 2H$_2$O (2.5);KH$_2$PO$_4$ (1.2); NaHCO$_3$ (25) and dextrose (11.1). The bathing solution is maintained at 37° C. and aerated with 95% O$_2$/5%CO$_2$. Tissues are connected via gold chains and stainless steel mounting wires to isometric force displacement transducers (Grass, Model FT03 D). Responses are recorded on a polygraph (Grass, Model 7E). One tissue from each animal serves as a time/solvent control and does not receive test compound.

Assay:

Rings are gradually stretched (over a 120 min. period) to a basal resting tension of 1 gm, which is maintained throughout the experiment. During the basal tension adjustment period, the rings are exposed to acetylcholine (ACH, 10$^{-6}$M) four times to verify tissue contractility. The tissues are then exposed to a submaximal dose of sulfated CCK-8 (Sigma, 3×10$^{-9}$M). After obtaining a stable response, the tissues are washed out 3 times rapidly and every 5 to 10 minutes for 1 hour to reestablish a stable baseline.

Compounds are dissolved in dimethylsulfoxide (DMSO), then diluted with water and assayed via a cumulative concentration-response curve to test compound (10$^{-11}$ to 3×10$^{-6}$M) followed by a concentration-response curve to sulfated CCK-8 (10$^{-11}$ to 10$^{-6}$M) in the presence of the highest dose of the test compound. As a final test, ACH (10 mM) is added to induce maximal contraction. A minimum of three determinations of activity are made for each test compound. Data for the products of Examples (1)–(19) are given in Table 1.

TABLE 1

| | In vitro Guinea Pig Gall Bladder |
|---|---|
| Example | % contraction (fold shift)[a] |
| 1 | 54.6% |
| 2 | 64.7% |
| 3 | 61.4% |
| 4 | (83-fold shift) |
| 5 | 37.9% |
| 6 | 56.9% |
| 7 | 15.6% |
| 8 | 51% |
| 9 | (14-fold shift) |
| 10 | 23.6% |
| 11 | 48.8% |
| 12 | 23.8% |
| 13 | (125-fold shift) |
| 14 | (10-fold shift) |
| 15 | (32-fold shift) |
| 16 | (62-fold shift) |
| 17 | 6% |
| 18 | 17.3% |
| Intermediate i | 12.2% |
| 19 | (6.8-fold shift) |

[a]% acetylcholine-induced maximum contraction for the test compound at 30mM or x-fold shift of the CCK-8 curve in the presence of the test compound (30mM).

18-HOUR DEPRIVATION-INDUCED FEEDING PARADIGM

Male, Long-Evans rats (Charles River Co., Raleigh, N.C.), weighing 300–375 grams, are acclimated individually for at least a week in hanging, stainless steel mesh cages (17.8×25.4×17.8 cm high) with ad libitum access to water (delivered through automatic drinking spouts at the rear of the cage) and food (Lab Blox, Purina Rodent Laboatory Chow #5001) on a 12-hour light-/dark cycle (lights on from 0600–1800 hours, or h) at approximately 22.8 C. Prior to testing, all chow, but not water, is removed at 1600 h. At 0900 h the next morning, rats are weighed. At 0945 h, rats are injected intraperitoneally (i.p.), orally (per os, or p.o.) or through an indwelling, intra-duodenal cannulea with a test compound or vehicle (2 mL/kg) and returned to their home cages. Food is presented at 1000 h. At 1030 h, remaining food and spillage is weighed.

GENERAL PROCEDURES

Unless otherwise noted, all starting materials were obtained from commercial suppliers and used without further purfication. The following solvents and reagents have been described by acronyms: tetrahydrofuran (THF), dimethylsulfoxide (DMSO), dichloromethane (DCM), trifluoroacetic acid (TFA), dimethylformamide (DMF), 1,1-carbonyldiimidazole (CDI), isobutylchloroformate (iBuCF), N-hydroxysuccinimide (HOBT), ethylcarbodiimide hydrochloride (EDC), bis(2-oxo-3-oxazolidinyl) phosphinic chloride (BOP), tert-butyloxycarbonyl (BOC), benzyloxycrbonyl (Cbz).

The $^1$HNMR spectra were recorded on either a Varian VXR-300 or a Varian Unity-300 instrument. Chemical shifts are expressed in parts per million (ppm, d units). Coupling constants are in units of hertz (Hz). Splitting patterns are designated as s, singlet; d, doublet; t, triplet; q, quartet; m, multiplat; b, broad.

Low-resolution mass spectra (MS) were recorded on a JEOL JMS-AX505HA, JEOL SX-102 or a SCIEX-APliii spectrometers. All mass spectra were taken in the positive ion mode under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Rotations were recorded on a Perkin-Elmer 241 polarimeter. All reactions were monitored by thin-layer chromatography on 0.25-mm E. Merck silica gel plates (60F-254), visualized with UV light, 7% ethanolic phosphomolybdic acid, or p-anisldehyde solution. Flash column chromatography was performed on silica gel (230–400 mesh, Merck).

Products were purified by preparative reversed phase-high pressure liquid chromatography (RP-HPLC) using a Waters Model 3000 Delta Prep equipped with a Delta-pak radial compression cartridge ($C_{18}$, 300 A, 15 m, 47 mm×300 mm). Linear gradients were used in all cases and the flow rate was 100 mL/minute ($t_o=5.0$ min). The solvent systems used are A:water, B:40:60, water:acetonitrile and C:acetonitrile. All solvents contained 0.1% trifluoroacetic acid (TFA). Analytical purity was assessed by RP-HPLC using a Waters 660E system equipped with a Waters 990 diode array spectrometer (t range 200–400 nM). The stationary phase was a Vydac $C_{18}$ column (5 m, 4.6 mm×250 mm). The flow rate was 1.5 mL/min ($t_o=3.0$ min) and the solvent systems were as described above. Data reported as tr, retention time in minutes (% $B_1$ to % $B_2$ in A over time).

CHEMISTRY

Intermediate Example A

2-Adamantyloxychloroformate

To a 0° C. solution of 2-adamantol (5.00 g, 32.84 mmol) in $CH_2Cl_2$ (82 mL) was added bis(trichloromethyl) carbonate (3.61 g, 12.15 mmol), followed by pyridine (2.66 mL, 32.84 mmol) in $CH_2Cl_2$ (61 mL). The reaction mixture warmed to room temprature and stirred for two hours. The solvent was removed in vacuo at 30° C., and the residue dissolved in ethyl acetate (160 mL) and stirred for 10 minutes. The pyridinium hydrochloride was removed by filtration and the solvent removed in vacuo at 30° C. to give an oil which solidified upon standing (6.42 g, 59%); IR ($CDCl_3$) 1770 cm$^{-1}$; $R_f$ (1:19, ethyl acetate:hexane)=0.68; $^1$HNMR (300 MHz, $CDCl_3$) d 5.00 (s, 1H), 2.18(s, 2H), 2.10–2.00 (m, 2H), 1.92–1.85 (m, 2H), 1.8(m, 4H), 1.55–1.65(m, 2H); IR ($CDCl_3$) 1770 cm$^{-1}$.

Intermediate Example B

2-Adamantyloxycarbonyl-N-hydroxy-succinimide

To Intermediate A (3.78 g, 17.7 mmol) dissolved in chloroform (34 mL) was added N-hydroxysuccinimide dicyclohexylamine salt (5.24 g, 17.7 mmol) in four equal portions. After stirring 2d, the reaction mixture was filtered and the precipitate washed with chloroform (60 mL). The filtrate was washed with 10% aqueous citric acid (20 mL), 10% aqueous sodium bicarbonate (20 mL), water (20 mL), dried ($MgSO_4$) and concentrated in vacuo to give the titled compound (4.09 g, 79%). $R_f$ (19:1 methylene chloride:methanol)=0.74; $^1$HNMR (300 MHz, $CDCl_3$) d 4.89 (s, 1H), 2.80 (s, 4H), 2.15 (s, 2H), 2.05–2.01 (d, J=12.9 Hz, 2H), 1.89–1.84 (m, 4H), 1.80–1.72 (m, 4H), 1.64–1.55 (m, 2H).

Intermediate Example C

2-Amino-3-(1H-indol-3-yl)-2R-methyl-propionic acid methyl ester

The titled compound was prepared by the method of Roeske and Anantharamaiah, *Tetrahedron Letters* (1982) 23, 33, 3335-3336. Physical and analytical data were consistent for the compound.

Intermediate Example D

2-Amino-3-(1H-indol-3-yl)-2S-methyl-prionic acid methyl ester

The titled compound was prepared by the method of Roeske and Anantharamaiah, *Tetrahedron Letters* (1982) 23, 33, 3335-3336. Physical and analytical data were consistent for the titled compound.

Intermediate Example E

2-[(Adamantan-2-yl-oxy)-carbonyl]-amino-3-(1H-indol-3-yl)-2RS-methyl-propionic acid To a-methyl-(D,L) tryptophan (0.50 g, 2.29 mmol) dissolved in dioxane (5 mL) was added 2-adamantyloxychloroformate (0.83 g, 2.51 mmol) and 1N aqueous NaOH (2.3 mL). The reaction mixture stirred 48 h, was acidified with 1N aqueous HCl and extracted with ethyl acetate (4×50 mL). The combined organic extracts were washed with brine (1×30 mL), dried (MgSO$_4$), and concentrated in vacuo to give the titled compound (1.049 g). R$_f$(9:1 methanol/methylene chloride)=0.58; $^1$H NMR (300 MHz, d6-DMSO) d 8.09 (s, 1H), 7.57 (d, J=8.06 Hz, 1H), 7.32 (d, J=8.06 Hz, 1H), 7.15 (t, J=7.82, Hz, 2H), 7.06 (t, J=7.82, 1H), 6.98 (s, 1H), 5.29 (s, 1H), 5.84 (s, 1H), 3.44 (s, 2H), 1.47-2.06 (m, 18H); MS (FAB) m/z 397 (MH+).

Intermediate Example F

2-[(Adamantan-2-yl-oxy)-carbonyl]-amino-3-(1H-indol-3-yL)-2R-methyl-prionic acid Step 1

To a solution of Intermediate A (0.308 g, 0.93 mmol) in dry THF (2.0 mL) was added a solution of Intermediate C (0.20 g, 0.75 mmol) in dry THF (3.5 mL) followed by a solution of triethylamine (0.21 mL, 1.50 mmol) in dry THF (3.5 mL) dropwise. After 2d, the reaction mixture was diluted with ethyl acetate (100 mL), washed with 1N aqueous NaOH (2×30 mL), 1N aqueous HCl (2×30 mL), brine (1×30 mL), dried (MgSO$_4$) and concentrated in vacuo to give the methyl ester of the titled compound (0.34 g). R$_f$(9:1, methylene chloride:methanol)=0.74; $^1$HNMR (300 MHz, CDCl$_3$) d 8.20 (s, 1H), 7.58 (m, 1H), 7.38 (m, 1H), 7.20-7.10 (m, 2H), 6.97 (s, 1H), 5.45 (s, 1H), 4.84 (m, 1H), 3.75 (s, 3H), 2.20-1.40 (m, 18H).

Step 2

To a solution of the ester from step 1 (0.31 g, 0.76 mmol) in aqueous 1,4-dioxane (1:1) (4 mL) was added lithium hydroxide (0.048 g, 1.10 mmol). The reaction mixture stirred at room temperature overnight. This mixture was acidified with 1N aqueous HCl and was extracted into ethyl acetate (6×30 mL). The combined organic extracts were washed with brine (1×30 mL), dried (MgSO$_4$) and concentrated in vacuo to give the titled compound (0.22 g, 73%). R$_f$(9:1, methylene chloride:methanol)=0.33; $^1$HNMR (300 MHz, CDCl$_3$) d 8.19 (s, 1H), 7.65 (d, J=8.06 Hz, 1H), 7.74-7.0 (m, 4H), 5.49 (s, 1H), 4.90 (s, 1H), 3.50 (s, 2H), 2.20-1.50 (m, 18H).

Intermediate Example G

2-[(Adamantan-2-yl-oxy)-carbonyl]-amino-3-(1H-indol-3-yl)-2S-methyl-propionic acid Step 1

To a solution of Intermediate D (0.80 g, 3.45 mmol) in chloroform (10 mL) was added Intermediate B (1.01 g, 3.45 mmol). The reaction mixture stirred overnight at room temperature. The precipitate was filtered and the filtrate was concentrated in vacuo. The resultant residue was dissolved in ethyl acetate (200 mL), washed with saturated aqueous sodium bicarbonate (2×30 mL), 1N aqueous HCl (2×30 mL), brine (1×30 mL), dried (MgSO$_4$) and concentrated in vacuo to give the methyl ester of the titled compound (1.34 g, 76%). R$_f$ (9:1, methylene chloride:methanol)=0.79.

Step 2

To a solution of the ester from Step 1 (1.34 g, 3.28 mmol) in aqueous 1,4-dioxane (1:1) (50 mL) was added excess lithium hydroxide (0.61 g, 14.45 mmol). The reaction mixture stirred at room temperature overnight. This mixture was partitioned between ethyl acetate (50 mL) and water (50 mL) and extracted into ethyl acetate (5×50 mL). The combined organic extracts were washed with 1N aqueous HCl (2×30 mL), brine (1×30 mL), dried (MgSO$_4$) and concentrated in vacuo to give the titled compound (1.097 g, 80%). R$_f$(9:1, methylene chloride:methanol)=0.31; $^1$HNMR (300 MHz, d6-DMSO) d 10.91 (s, 1H), 7.42 (d, J=8.0 Hz, 1H), 7.30 (d, J=8.0 Hz, 1H), 7.02 (m, 2H), 6.99 (m, 1H), 4.67 (s, 1H), 4.51 (d, J=3 Hz, 1H), 3.63 (s, 1H), 3.30 (obscure ABq, 2H), 2.02-1.20 (m, 18H).

Intermediate Example H

2R-[(Adamantan-2-yl-oxy)-carbonyl]-amino-3-(1H-indol-3-yl)-propionic acid

To a solution of Intermediate B (1.19 g, 4.06 mmol) in THF (60 mL) was added a solution of D-tryptophan (0.83 g, 4.06 mmol) in 10% aqueous sodium carbonate (20 mL) and THF (10 mL). The reaction mixture stirred overnight at room temperature, was acidified with 1N aqueous HCl and extracted into ethyl acetate (6×50 mL). The combined organic extracts were washed with water (1×30 mL), brine (1×30 mL), dried (MgSO$_4$) and concentrated in vacuo to give the titled compound (1.66 g, quant.). R$_f$(9:1, methylene chloride:methanol)=0.24; $^1$HNMR (300 MHz, CDCl$_3$) d 7.56 (d, J=8.0 Hz, 1H), 7.32 (d, J=8.0 Hz, 1H ), 7.10-6.98 (m, 3H), 4.68 (s, 1H), 4.09 (m, 1H), 3.20-3.0 (m, 1H), 2.20-1.40 (m, 15H).

Intermediate Example J

2S-[(Adamantan-2-yl-oxy)-carbonyl]-amino-3-(1H-indol-3-yl)-propionic acid

The procedure as described for Intermediate Example H was followed, hence, L-tryptophan (1.19 g, 4.06 mmol) gave the titled product (1.53 g, 94%). R$_f$(9:1, methylene chloride:methanol)=0.24; $^1$HNMR (300 MHz, CDCl$_3$) d 7.53 (d, J=8.0 Hz, 1H), 7.30 (d, J=8.0 Hz, 1H), 6.96-7.08 (m, 3H), 4.65 (s, 1H), 4.46-4.06 (m, 1H), 3.20-3.0 (m, 1H), 2.20-1.40 (m, 15H).

Intermediate Example K

2-[(Benzyloxy)-carbonyl]-amino-3-(1H-indol-3-yl)-2RS-methyl propionic acid

To a solution of D,L-a-methyl tryptophan (5.00 g, 0.021 mol) in 10% aqueous acetone (100 mL) and sodium carbonate (2.25 g, 0.021 mol) was added benzyloxycarbonyl-N-hydroxysuccinimide (5.29 g, 0.021 mol) in acetone (50 mL). The solution was stirred overnight. The pH was adjusted to 4 with 1N aqueous HCl, and the solution was concentrated in vacuo. The residue was partitioned between ethyl acetate (500 mL) and aqueous 1N HCl (300 mL), and the organic layer was separated, washed with water (500 mL), dried (Na$_2$SO$_4$) and concentrated in vacuo to give a white solid (6.9 g, 0.019 mol) which was used without further purification. R$_f$ (9:1, methylene chloride:methanol)=0.16; MS (FAB) m/e 353 (MH+).

Intermediate Example L

2-[(t-Butyloxy)-carbonyl]-amino-3-(1H-indol-3-yl)-2RS-methyl-propionic acid

Intermediate L was prepared analogously to Intermediate E. Hence to a-methy-D,L-tryptophan (2.18 g, 10.0 mmol) was added di-tert-butyldicarbonate (2.40 g, 11.0 mmol) to give the titled product (2.25 g, 76%). R$_f$(9:1, methylene chloride:methanol)=0.24; $^1$HNMR (300 MHz, CDCl$_3$) d 7.45 (d, J=8.0 Hz, 1H), 7.30 (d, J=8.0 Hz, 1H), 7.02–6.90(m, 3H), 3.10 (obscured ABq, 2H), 1.38 (s, 9H), 1.25 (s, 3H).

Intermediate Example M

2-[(t-Butyloxy)-carbonyl]-amino-3-(1H-indol-3-yl)-2RS-methyl-propionic acid

Intermediate M was prepared analogously to Intermediate E. Hence, Intermediate C (227.0 mg, 0.85 mmol) gave the titled product. R$_f$(9:1, methylene chloride:methanol)=0.24.

Intermediate Example N

N-Adamantan-2-yl-2-amino-3-(1H-indol-3-yl)-2RS-methyl-propionicamide

Step 1

To a solution of Intermediate K (0.352 g, 0.001 mol), 2-aminoadamatane (0.187 g, 0.001 mol), N-hydroxybenztriazole (0.135 g, 0.001 mol), and triethylamine (0.140 mL, 0.001 moles) in dichloromethane (35 mL) was added EDC (0.191 g, 0.001 mol). The solution was allowed to stir at room temperature overnight. The reaction mixture was diluted with dichloromethane (200 mL) and extracted successively with 1N aqueous HCl (100 mL), water (100 mL), 10% aqueous sodium bicarbonate (100 mL) and water (100 mL), then dried (Na$_2$SO$_4$) and evaporated to give the crude amide (0.390 g, 0.75 mmol) which was used without further purification. R$_f$ (9:1, methylene chloride:methanol)=0.78; MS (FAB) 486 (MH+).

Step 2

The amide from step 2 (0.39 g, 0.75 mmol) was dissolved in MeOH (5 mL) and glacial acetic acid (1 mL) and 10% Pd/C (50 mg) was added. The mixture was shaken at 50 psi until the reaction was judged complete by TLC. The mixture was filtered through a celite pad, and the pad was washed with methanol (100 mL). The methanol was evaporated in vacuo and the residue partitioned between ethyl acetate (50 mL) and 1N aqueous NaOH (50 mL). The organic layer was separated, washed with water (100 mL), dried (Na$_2$SO$_4$) and evaporated to give the product as a white foam (0.27 g, 0.7 mmol) which was used without further purification. R$_f$ (9:1, methylene chloride:methanol)=0.18; MS (FAB) m/e 352 (MH+).

Intermediate Example O 1-(6-Amino-5R-[(t-Butyloxy)carbonyl]-amino-hexyl)-3-o-tolyl-urea Step 1

To N-a-BOC-D-lysine (5.0 g, 20.48 mmol) dissolved in 1N aqueous sodium hydroxide (20.48 mmol) was added o-toluylisocyanate (2.53 mL, 20.48 mmol). The reaction mixture stirred 3 h, was acidified with 1N aqueous HCl and extracted into ethyl acetate is (6×50 mL). The combined organic extracts were washed with brine (1×30 mL), dried (MgSO$_4$) and concentrated in vacuo to give 7.93 g of crude urea. R$_f$(9:1, methanol:methylene chloride)=0.06; 1H NMR (300 MHz, d6-DMSO) d 7.81 (d, J=8.06 Hz, 1H), 7.58 (s, 1 H) 7.08 (m, 3H), 6.83 (t, J=7.33 Hz, 1H), 6.51 (t, J=4.88 Hz, 1H), 3.83 (m, 1H), 3.05 (d, J=5.13 Hz, 2H), 2.15 (s, 3H), 1.36 (s, 13H); MS (EI) m/z 380 (MH+).

Step 2

To the crude urea from step 1 (1.98 g, 5.22 mmol) dissolved in THF (47 mL) was added 1,1-carbonyldiimidazole (1.69 g, 10.4 mmol). The reaction mixture stirred 16 h at room temperature. This mixture was cooled to 0° C. and a solution of lithium aluminum hydride (26.1 mL of a 1M THF solution) was added dropwise. After 2 h 2N aqueous NaOH was added dropwise and the aqueous layer was extracted with ethyl acetate (4×50 mL). The combined organic extracts were washed with 1N aqueous HCl (1×30 mL), brine (1×30 mL), dried (MgSO$_4$) and concentrated in vacuo to give (1.00 g, 52%) of the product alcohol: R$_f$ (9:1, methanol:methylene chloride)=0.60; $^1$ HNMR (300 MHz, d6-DMSO) d 7.79 (d, J=8.1 Hz, 1H), 7.52 (s, 1H), 7.01–7.08 (m, 2H), 6.79–6.84 (m,1H), 6.42–6.50 (m, 2H), 4.54 (m, 1H), 3.15–3.29 (m, 2H), 3.04 (m, 2H), 2.13 (s, 3H), 1.34 (s, 9H), 1.29–1.52 (m, 6H); MS (FAB) mlz 366 (MH+).

Alternative procedure for formation of 2

To the crude urea from step 1 (7.9 g, 20.9 mmol) in THF (210 mL) cooled to 0° C. was added isobutyl chloroformate (3.3 mL, 25.1 mmol) and diisopropylethylamine (4.5 mL, 25.1 mmol). The reaction mixture stirred 1 h at 0° C. and then was added to a THF (210 mL) slurry of lithium aluminum hydride (1.59 g). The reaction stirred 48 h at room temperature, was acidified with 1N aqueous HCl and diluted with ethyl acetate (500 mL). The reaction mixture was filtered through a pad of celite and the filtrate was extracted with ethyl acetate (3×100 mL) washed with brine (1×50 mL), dried (MgSO$_4$) and concentrated in vacuo. Purification by flash chromatography (SiO$_2$ 1.1, hexanes:ethyl acetate) gave (4.18 g, 55%) of the product alcohol.

Step 3

To a solution of the product alcohol of step 2 (4.00 g, 10.96 mmol) and triethylamine (1.83 mL, 13.15 mmol) dissolved in methylene chloride (22 mL) and cooled to 0° C. was added methanesulphonyl chloride (1.02 mL, 13.15 mmol) dropwise. The reaction mixture stirred at room temperature overnight. The resultant mixture was diluted with methylene chloride, washed with aqueous citric acid (2×30 mL), water (1×30 mL), brine (1×30 mL), dried (MgSO$_4$), and concentrated in vacuo. Purification by stepwise flash chromatography (SiO₂ 50% hexanes:ethyl acetate, then 30% hexanes:ethyl acetate) gave 1.78 g of the product mesylate: $R_f$ (1:1 hexanes:ethyl acetate),=0.16 (9:1, methanol:methylene chloride)=0.55; ¹HNMR (300 MHz, d6-DMSO) d 7.79 (d, J=8.1 Hz, 1H), 7.54 (s, 1H), 7.01–7.09 (m, 2H), 6.80–6.91 (m, 2H), 6.50–6.51 (m, 1H), 3.99–4.10 (m, 2H), 3.63 (s, 1H), 3.13 (s, 3H), 3.04–3.07 (m, 2H), 2.14 (s, 3H), 1.33 (s, 9H), 1.25–1.49 (m, 6H); MS (FAB) m/z 444 (MH+).

Step 4

To the product mesylate of step 3 (1.78 g, 4.0 mmol) dissolved in dimethylformamide (40 mL) was added sodium azide (0.52 g, 8.00 mmol). The reaction mixture was heated at 80° C. for 2 h, then poured into ice water and extracted with ethyl acetate (3×50 mL). The combined organic extracts were washed with water (3×30 mL), dried (MgSO₄) and concentrated in vacuo. Purification by flash chromatography (SiO₂, 1:1, hexanes:ethyl acetate) gave (0.68 g, 44%) of the product azide: $R_f$ (1:1 , hexanes:ethyl acetate)=0.22; ¹HNMR (300 MHz, d6-DMSO) d 7.79 (d, J=7.8 Hz, 1H), 7.53 (s, 1H), 7.02–7.09 (m, 2H), 6.80–6.88 (m, 2H), 6.49 (m, 1H), 3.52 (s,1H), 3.22 (d, J=5.9 Hz, 2H), 3.04 (m, 2H), 2.14 (s, 3H), 1.23–1.43 (m, 6H), 1.34 (s, 9H); MS (FAB) m/z 391 (MH+).

Step 5

To the product azide of step 4 (0.68 g, 1.7 mmol) dissolved in ethanol (10 mL) was added 10% palladium on carbon (68 mg). The reaction mixture was stirred under 1 atmosphere of hydrogen for 12 h, filtered through a pad of celite and concentrated in vacuo. Purification by flash chromatography (SiO₂, 1:9, methanol:methylene chloride) gave (0.59 g, 95%) of product amine: $R_f$ (1:9, methanol:methylene chloride)=0.15; ¹HNMR (300 MHz, d6-DMSO) d 7.79 (d, J=8.06 Hz, 1H), 7.53 (s, 1H), 7.02–7.09 (m, 2H), 6.82 (t, J=7.3 Hz, 1H), 6.48–6.50 (m, 2H), 3.31 (s, 3H), 3.0 (m, 2H), 2.43 (d, J=6.1 Hz, 2H), 2.14 (s, 3H), 1.35 (s, 9H), 1.23–1.56 (m, 6H); MS (ESI) m/z 365 (MH+).

Intermediate Example P 1-(6-Amino-5S-[(t-Butyloxy)carbonyl]-amino-hexy)-3-o-tolyl-urea Intermediate P was prepared analogously to Intermediate O. Hence, N-a-t-butyloxycarbonyl-L-lysine (5.42 g, 14.3 mmol) gave the enantiomeric compound (115.0 mg, 2%).

Intermediate Example Q

N-6-[(Benzyloxy)carbonyl]-N-2-[(t-Butyloxy)carbonyl]-hexane-1,2R,6-triamine

Intermediate Q was prepared analogously to Intermediate O. Hence, N-a-t-butyloxycarbonyl-N-e-benzyloxycarbonyl-D-lysine (4.90 g, 12.9 mmol) gave the product (1.31 g, 28%). $R_f$ (9:1, methylene chloride:methanol)=0.2; ¹HNMR (300 MHz, d6 DMSO) d 7.25–7.37 (m, 5H), 7.17–7.20 (m, 1H), 6.46 (d, J=8.5 Hz, 1H), 4.97 (s, 2H), 2.97–2.91 (m, 2H), 2.42 (d, J=5.9 Hz, 2H), 1.35 (s, 9H), 1.4–1.16 (m, 6H). (In CDCl₃ broad peak seen at 3.53 ppm for methine); MS (ESI) m/z 366 (MH+)

Intermediate Example R

3R-[(t-Butyloxy)carbonyl]-amino-7-(3-o-tolyl-ureido)-heptanoic acid

Step 1

To a solution of 2-[(t-butyloxy)carbonyl]-amino-6-(3-o-tolyl-ureido)-hexanoic acid (3.8 g, 0.01 mol) and N-methylmorpholine (1.1 mL, 0.01 mol) in tetrahydrofuran (100 mL) at −15° C. was added isobutylchloroformate (1.3 mL, 0.01 mol) in tetrahydrofuran (20 mL). The mixture was stirred 1 h at 0° C., whereupon a solution of freshly prepared diazomethane in ether was added until a persistent yellow color was obtained. The resultant solution was allowed to stir overnight, then the residual diazomethane was quenched by the addition of glacial acetic acid. The tetrahydrofuran was evaporated in vacuo and the residual yellow oil was partitioned between ethyl acetate (300 mL) and saturated aqueous NaHCO₃ (300 mL). The organic layer was separated, washed with water (300 mL), dried (MgSO₄) and concentrated in vacuo. The crude diazomethylketone (3.5 g) was purified by chromatography over silica gel (hexane:ethyl acetate, 1:1) to give 1.0 g of a bright yellow solid. $R_f$(3:1, ethyl acetate:hexane)=0.33 ; ¹HNMR (CD₃OD):delta=6.1 (1H, CH=N₂); MS (FAB) m/e 404 (MH+).

Step 2

The diazomethylketone from step 1 (1.9 g, 4.7 mmol) was dissolved in MeOH (50 mL) and silver benzoate (0.072 g, 4.7 mmol) in triethylamine (1 mL) was added. After the evolution of N₂ was complete, a second portion of silver benzoate was added, and the solution was allowed to stir for 1 h at room temperature, whereupon activated charcoal (0.5 gm) was added, and the solution was filtered by gravity. The filtrate was concentrated in vacuo, and partitioned between ethyl acetate (300 mL) and 10% aqueous citric acid (300 mL). The organic layer was separated, washed with water (300 mL), dried (Na₂SO₄) and concentrated in vacuo to give 1.84 grams of the beta-amino ester which was used in the following step without further purification. $R_f$(3:1, ethyl acetate:hexane)=0.44; MS (FAB) m/e 408 (MH+); NMR (d6-DMSO): delta=3.62 (s, 3H, CH₂COOCH₃) 2.43 (d, 2H, CH₂COOCH₃)

Step 3

The b-amino ester from step 2 (1.84 g, 4.7 mmol) was dissolved in methanol (50 mL) and water (2 mL) and 6N aqueous NaOH (0.8 mL) was added. The solution was allowed to stir overnight, then neutralized with 1N HCl, and concentrated in vacuo. The residual oil was partitioned between 10% aqueous sodium bicarbonate (300 mL) and ethyl acetate (300 mL). The organic layer was separated and washed with water (300 mL). The aqueous layer was extracted twice with ethyl acetate (300 mL). The organic layers were combined, washed with water (300 mL), dried (Na₂SO₄) and concentrated in vacuo to give 1.7 g of the product b-amino acid as an amorphous solid. $R_f$(250:25:1, methylene chloride: methanol:acetic acid)=0.29; MS (FAB): m/e=394 (MH+).

Intermediate Example S 1-(6-Amino-5S-[(benzyloxy)carbonyl]-amino hexyl)-3-o-tolyl-urea Step 1

To aqueous sodium hyroxide (36.0 mL, 36.0 mmol) was added to N-a-Cbz-lysine (10.00 g, 36.0 mmol). The resultant mixture stirred at room temperature for 5 min prior to the addition of o-tolylisocyanate (3.90 mL, 36.0 mmol). The resultant mixture was stirred at room temperature for 18 h. During this time the reaction mixture turned solid. The resultant solid was dissolved in water (50 mL) and the pH was adjusted to 2.0 with concentrated hydrochloric acid to precipitate a flocculant white gum. The product was extracted into ethyl acetate (3×60 mL). The resultant organic extracts were washed with water (2×50 mL), dried (MgSO$_4$) and concentrated in vacuo to afford product as a white glassy solid (14.0 g). [a]$_D$ (C=0.0152, methanol)=−2.69°; $^1$HNMR (300 MHz, d6-DMSO) d 7.8 (d,1H), 7.60 (d, 2H), 7.38 (b, 5H), 7.08 (m, 2H), 6.82 (t, 1H), 6.50 (t, 1H), 5.0 (s, 2H), 3.03 (b, 2H), 2.18 (s, 3H), 1.5–1.8 (m, 2H), 1.40 (b, 4H).

Step 2

A solution of the above compound (9.50 g, 22.8 mmol) and 1,1-carbonyl-diimidazole (5.16 g, 34.2 mmol) was stirred at room temperature for 16 h. Sodium borohydride (4.14 g, 114.0 mmol) was added and the resultant mixture stirred vigorously at room temperature for 1.5 h prior to the addition of a further batch (1.00 g) of sodium borohydride. The resultant mixture was stirred vigorously at room temperature for a further 3 h, then neutralized with 2N aqueous hydrochloric acid pH6. The resultant mixture was extracted into ethyl acetate (3×100 mL), the combined organic extracts were washed with 2N aqueous sodium hydroxide (2×50 mL), water (50 mL), brine (50 mL), dried (MgSO$_4$) and concentrated in vacuo to afford the product as a white solid (7.40 g). [a]$_D$ (C=0.0026, methanol)=−8.88°; $^1$HNMR (300 MHz, d6-DMSO) d 7.8 (d, 1H), 7.58 (s, 1H), 7.38 (b, 5H), 7.68 (m, 2H), 6.83 (t, 1H), 6.51 (t, 1H), 4.98 (s, 2H), 4.60 (b, 1H), 3.2–3.4 (b, 2H), 2.18 (s, 3H), 1.2–1.6 (b, 6H);

Step 3

To a solution of the product above (7.10 g, 17.77 mmol), in dichloromethane (100 mL) was added triethylamine (3.69 mL, 26.52 mmol), tosylchloride (3.39 g, 17.75 mmol) and N,N-dimethylaminopyridine (20 mg). The resultant reaction mixture was stirred at room temperature for 16 h, washed with 2N aqueous sodium hydrogen carbonate (100 mL), 0.5N aqueous citric acid (50 mL), and water (50 mL) prior to drying (MgSO$_4$) and concentration in vacuo to afford the product (8.84 g) as a white foam which was used crude in the next reaction. R$_f$ (9:1 methylene chloride:methanol)=0.52; $^1$HNMR (300 MHz, CDCl$_3$) d 7.80 (d, 2H), 7.10–7.40 (m, 15H), 6.03 (s, 1H), 5.03 (s, 2H), 4.01 (d, 2H), 3.80 (b, 1H), 3.20 (b, 2H), 2.41 (s, 3H), 2.21 (s, 3H), 1.2–1.6 (m, 6H).

Step 4

A mixture of the product from step 3 (8.84 g, 15.96 mmol) and sodium azide (2.06 g, 31.98 mmol) in N,N-dimethylformamide (120 mL) was heated at 80° C. for 1.25 h. The reaction mixture was cooled, poured into water (150 mL) and extracted into ethyl acetate (3×100 mL). The combined organics were washed with water (100 mL), brine (100 mL), dried (MgSO$_4$) and concentrated in vacuo to afford the product (6.70 g) as a white foam which was used crude in the next reaction. R$_f$(2:1, ethylacetate:hexane)=0.48; $^1$HNMR (300 MHz, CDCl$_3$) d 7.05–7.4 (b, 11H), 6.02 (s, 1H), 5.03 (s, 2H), 3.40 (b, 2H), 3.20 (b, 2H), 2.21 (s, 3H), 1.2–1.6 (m, 6H).

Step 5

A mixture of the product above (6.70 g, 15.58 mmol), Lindlar catalyst (2.68 g) and ethyl acetate (150 mL) was shaken under 50 psi hydrogen using a Parr hydrogenation apparatus. After 5 h the solids were removed by filtration through a pad of celite, the filtrate concentrated in vacuo and the resultant residue partitioned between dichloromethane (100 mL) and 2N aqueous hydrochloric acid (3×50 mL). The combined aqueous phase was then adjusted to pH7 with solid sodium hydrogen carbonate and then to pH 10 with 2N aqueous sodium hydroxide and extracted into methylene choloride (3×80 mL). The combined organic extracts were dried s (MgSO$_4$/K$_2$CO$_3$) and concentrated in vacuo to afford the product (900 mg) as a cream solid. A solid that precipitated from the aqueous phase was isolated by filtration and dried by azeotrope with acetonitrile to afford additional product (710 mg). The titled product was used crude in the next reaction. R$_f$(9:1:0.2, methylene chloride:methanol:triethylamine)=0.31; $^1$HMNR (300 MHz, CDCl$_3$) d 7.59 (d, 2H), 7.0–7.4 (m, 8H), 6.58 (s, 1H), 5.31 (b, 2H), 5.03 (s, 2H), 3.6 (b, 1H), 3.20 (b, 2H), 2.62 (ddd, 2H), 2.21 (s, 3H), 1.2–1.6 (m, 6H).

Intermediate Example T 1-(6-Amino-5R-[(benzyloxy)carbonyl]-amino hexyl)-3-o-tolyl-urea This was prepared in a manner analogous to intermediate S. Hence, N-a-Cbz-D-lysine (10.00 g, 36 mmol) gave the product (1.00 g) as an off white solid. R$_f$ (9:1:0.2, methylene chloride:methanol:triethylamine)=0.31; $^1$HNMR (300 MHz, d6 DMSO) d 7.82 (d, 1H), 7.63 (s, 1H), 7.3–7.4 (m, 4H), 7.03 (m, 2H), 6.81 (t, 1H), 6.62 (t, 1H), 5.0 (apparent q, 2H), 3.60 (b, 2H), 3.02 (b, 2H), 2.18 (s, 3H), 1.2–1.6 (b, 6H); [a]$_d$ (c=0.01285, MeOH)=+2.68°; MS (ESI) m/z, 389 (MH+).

Intermediate Example U 1-(5-Amino-4R-[(benzyloxy)carbonyl]-amino pentyl)-3-o-tolyl-urea Step 1

A solution of N-d-BOC-D-ornithine (4.0 g, 10.9 mmol) in 4N HCl in dioxane (40 mL) was stirred at room temperature for 1.5 h. The solids that formed were removed by filtration, washed with ether and dried under vacuum to afford the product (3.11 g) as a white powder. $^1$HNMR (300 MHz, d6-DMSO) d 8.0 (b, 3H), 7.42 (d, 1H), 7.38 (s, 5H), 3.98 (b, 1H), 2.78 (b, 2H), 1.5–1.8(m, 2H).

Step 2

This was prepared as for step 1 of intermediate S. Hence the material from step 1 (3.11 g, 10.28 mmol) gave the product (3.48 g) as a white solid. $^1$HNMR (300 MHz, d6-DMSO) d 7.8 (d, 1H), 7.60 (d, 1H), 7.56 (s, 1H), 7.38 (b, _H), 7.06 (m, 2H), 6.83 (t, 1H), 6.50 (t, 1H), 5.01 (s, 2H), 3.95 (dt, 1H), 3.02 (b, 2H), 2.10 (s, 3H), 1.4–1.8(b, 4H).

Step 3

This was prepared in a similar manner to step 2 of intermediate S. Hence the material from step 2 (3.48 g, 8.72 mmol) gave the product (3.23 g) as a white solid. R$_f$ (9:1:0.1, methylene chloride:methanol:triethylamine)=0.78; $^1$HNMR (300 MHz, CDCl$_3$+d6 DMSO, 20:1) d 7.61 (d, 2H), 7.3 (b, 5H), 7.10 (m, 2H), 6.90 (m, 3H), 5.8 (b, 1H), 5.75 (d, 1H), 5.0 (s, 2H), 3.16 (b, 2H), 2.19 (s, 3H), 1.4–1.5 (b, 4H); MS (ESI) m/z 386.4 (MH+).

Step 4

This was prepared in a similar manner to step 3 of intermediate S. Hence the material from step 3 (3.22 g, 8.35 mmol) gave the product (4.25 g) as a cream foam that was used crude in the next reaction. $R_f$ (9:1 methylene chloride:methanol)=0.51; $^1$HNMR (300 MHz, d6-DMSO) d 7.78 (m, 3H), 7.55 (s, 1H), 7.40 (d, 2H), 7.36 (b, 6H), 7.04 (m, 2H), 6.82 (t, 1H), 6.50 (t, 1H), 4.98 (s, 2H), 3.96 (d, 2H), 3.04 (b, 1H), 3.0 (b, 2H), 2.40 (s, 3H), 2.18 (s, 3H), 1.40 (b, 4H).

Step 5

This was prepared in a similar manner to step 4 of intermediate S. Hence the material from step 4 (4.25 g, 7.88 mmol) gave the product (2.51 g) as a white powder which was used crude in the next step. $R_f$ (2:1 ethyl acetate:hexane)=0.47; $^1$HNMR (300 MHz, d6-DMSO) d 7.8 (d, 1H), 7.55 (s, 1H), 7.38 (b, 6H), 7.05 (m, 2H), 6.82 (t, 1H), 6.50 (t, 1H), 5.02 (s, 2H), 3.61 (b, 1H), 3.25 (b, 2H), 3.03 (b, 2H), 2.15 (s, 3H), 1.40 (b, 4H).

Step 6

This was prepared in a similar manner to step 5 of intermediate S except that tetrahydrofuran was the sovent. Hence the material from step 5 (1.25 g) gave the product (693 mg) as a white solid. $R_f$ (9:1:0.1, methylene chloride:methanol:triethylamine)=0.22; $^1$HNMR (300 MHz, d6-DMSO) d 7.80 (d, 1H), 7.62 (s, 1H), 7.38 (b, 1H), 7.06 (apparent q, 3H), 6.84 (t, 1H), 6.60 (b, 1H), 5.0 (s, 2H), 3.25 (b, 2H), 2.15 (s, 3H), 1.40 (b, 4H); MS (ESI) m/z 385.4 (MH+).

Intermediate Example V 1-(5-Amino-4S-[(benzyloxy)carbonyl]-amino-pentyl)-3-o-tolyl-urea This was prepared in a similar manner to intermediate U. Hence N-a-Cbz-L-ornithine (5.00 g, 18.7 mmol) gave the product (1.31 g) as a white glassy foam after flash column chromatography (95:5:0.1, methylene chloride:triethylamine). $R_f$ (1% Et$_3$N, 10% MeOH, CH$_2$Cl$_2$)=0.22; $^1$HNMR (300 MHz, d6-DMSO) d 7.80 (d, 1H), 7.60 (s, 1H), 7.38 (b, 6H), 7.06 (m, 3H), 6.84 (t, 1H), 6.60 (b, 1H), 5.0 (s, 2H), 3.25 (b, 2H), 3.0 (d, 2H), 2.15 (s, 3H), 1.40 (b, 4H); MS (ESI) m/z 385.4 (MH+).

Intermediate Example W 1-(5-Amino-4S-[(benzyloxy)carbonyl]-amino-pentyl)-3-o-tolyl-urea Step 1

This was prepared in a similar manner to step 1 of intermediate S. Hence N-a-BOC-L-ornithine (5.0 g, 21.55 mmol) gave the product (5.63 g) as a white foam. $^1$HNMR (300 MHz, d6-DMSO) d 7.8 (d, 1H), 7.58 (s, 1H), 7.08 (m, 2H), 6.82 (t, 1H), 6.50 (t, 1H), 3.83 (dt, 1H), 3.02 (m, 2H), 2.17 (s, 3H), 1.4–1.7 (m, 4H), 1.30 (s, 9H); MS (ESI) m/z 729.2 (MH)+$_2$.

Step 2

This was prepared in a similar manner to step 2 of intermediate S. Hence the material from step 1 (5.63 g, 15.40 mmol) gave the product (3.34 g) as a white solid after flash column chromatography (95:5, methylene chloride:methanol). $R_f$ (9:1, methylene chloride:methanol)=0.27; $^1$HNMR (300 MHz, d6-DMSO) d 7.8 (d, 1H), 7.58 (s, 1H), 7.04 (m, 2H), 6.81 (b, 2H), 4.60 (b, 1H), 3.25 (b, 2H), 2.15 (s, 3H), 1.2–1.6 (c+s, 13H).

Step 3

This was prepared in a similar manner step 3 of intermediate S. Hence the above product (2.84 g, 8.09 mmol) gave the titled product (3.08 g, 80% pure). This mixture was used crude in the following reaction. $R_f$ (9:1, methylene chloride:methanol)=0.52; $^1$HNMR (300 MHz, d6-DMSO) d 7.80 (m, 3H), 7.50 (s, 1H), 7.44 (d, 1H), 7.08 (m, 3H), 6.82 (m, 2H), 6.48 (m, 2H), 3.90 (b, 2H), 3.60 (b, 1H), 3.0 (b, 2H), 2.50 (s, 3H), 2.10 (s, 3H), 1.1–1.4(m, 13H).

Step 4

This was prepared in a similar manner to step 4 from intermediate S. Hence the product from step 3 (3.08 g, 6.09 mmol) gave the product (940 mg) as a colorless glass which contained about 10% impurities. This material was used crude in the following reaction. $R_f$ (9:1, methylene chloride:methanol)=0.50; $^1$HNMR (300 MHz, d6-DMSO) d 7.80 (d, 1H), 7.50 (s, 1H), 7.05 (m, 2H), 6.81 (t, 1H), 6.50 (b, 2H), 3 (b, 1H), 3.22 (2dd, 2H), 3.03 (b, 2H), 2.08 (s, 3H), 1.1–1.6 (m, 13H); MS (ESI) m/z 3.77.4 (MH+).

Step 5

A mixture of the above compound (940 mg) and 10% palladium on carbon (95 mg) in ethanol (50 mL) was stirred under an atmosphere of hydrogen for 20 h. The solids were removed by filtration through celite and the filtrate was concentrated in vacuo. The residue was partitioned between ethyl acetate (50 mL) and 10% aqueous citric acid (3×50 mL). The combined aqueous extracts were washed with ethyl acetate (50 mL), the pH adjusted to pH11 (2N aqueous sodium hydroxide) and extracted into ethyl acetate. The latter combined organic extracts were washed with water, brine, dried (K$_2$CO$_3$) and concentrated in vacuo. The residue was purified by flash column chromatography (9:1:0.1, methylene chloride:methanol:ammonia) to afford the product (80 mg) as a clear colorless foam. $R_f$ (9:1:9.1, methylene chloride:methanol:ammonia)=0.22; $_1$HNMR (300 MHz, CDCl$_3$) d 7.50 (b, 1H), 7.20 (b, 3H), 7.03 (b, 1H), 6.40 (s, 1H), 5.30 (b, 1H), 4.80 (d, 1H), 3.58 (b, 1H), 3.20 (b, 2H), 2.62 (2dd, 2H), 2.22 (s, 3H), 1.1–1.5 (mm, 13H); MS (ESI) m/z 351.4 (MH+).

EXAMPLE 1

N-[1-R-[2-Adamantan-2-yl-oxy)carbonyl]-amino-3-(1H-indol-3-yl)-2RS-methyl-propionylamino-methyl]-5-(3-o-tolyl-ureido)-pentyl]-succinamic acid Step 1

To Intermediate O (0.17 g, 0.47 mmol) dissolved in dimethylformamide (2 mL) and methylene chloride (2 mL) was added 1-hydroxybenztriazole (0.19 g, 1.40 mmol), Intermediate E (0.19 g, 0.93 mmol), and 1-(3-dimethylaminopropyl)-3-ethylcarbodiimide hydrochloride (0.22 g, 1.12 mmol). The reaction mixture stirred at room temperature for 24 h, was diluted with ethyl acetate, extracted with saturated aqueous NaHCO$_3$ (2×30 mL), 1N aqueous HCl (2×30 mL), brine (1×30 mL), dried (MgSO$_4$), and concentrated in vacuo to give the coupled product (0.53 g).

Step 2

The product of step 1 was dissolved in 4N HCl in dioxane (5 mL) and stirred for 1 h at room temperature. The reaction mixture formed a gum on addition of ethyl ether. The ethyl ether was decanted and the gum triturated with ethyl ether (3×30 mL) to give 0.22 g of the amine hydrochloride salt (0.32 mmol, 69% 2-steps); $R_f$ (9:1, methylene chloride:methanol)=0.14; $^1$HNMR (300 MHz, CD$_3$OD) d 7.40 (t, J=8.32 Hz, 2H), 7.23 (d, J=7.82 Hz, 1H), 6.88–7.06 (m, 6H), 3.00–3.31 (m, 5H), 2.15 (s, 3H), 1.30 1.94 (m, 24H); MS (FAB) m/z 643 (MH+).

Step 3

To the product of step 2 (0.20 g, 0.31 mmol) dissolved in dimethylformamide (0.62 mL) was added triethylamine (86 mL, 0.62 mmol) and succinic anhydride (40 mg, 0.40 mmol). The reaction mixture stirred overnight, was diluted with MeOH/CH3CN/H2O and purified by preparative RP-HPLC chromatography (60–90% B in A, 30 min) to give the product (15.3 mg, 7%). The diastereomers were >98% pure and had minimal separation as determined on analytical RP-HPLC: tr=19.0 min (70–100% B in A, 30 min). MS (FAB) m/z 743 (MH+).

EXAMPLE 2

N-[1R-[2-Adamantan-2-yl-oxy)carbonyl]-amino-3-(1H-indol-3-yl)-2R-methyl-propionylamino-methyl]-5-(3-o-tolyl-ureido)-pentyl]-succinamic acid Example 2 was prepared analogously to Example 1. Hence Intermediate F (200.0 mg, 0.05 mmol) was coupled to Intermediate O (182.0 mg, 0.05 mmol) to give the product (69.4 mg, 19%) after preparative RP-HPLC purification (60–90% B, 30 min). The lyophile was >98% pure as determined on analytical RP-HPLC: tr=28.9 min (60–90% B in A, 30 min). $R_f$ (10:1:0.1, methylene chloride:methanol:acetic acid)=0.27; $^1$HNMR (300 MHz, CD$_3$OD) d 7.50 (d, J=8.0 Hz, 2H), 7.31 (d, J=8.0 Hz, 1H), 7.20–6.90 (m, 6H), 3.88 (s, 1H), 3.50 (m, 2H), 3.21 (m, 3H), 3.0 (m, 1H), 2.58–2.45 (m, 4H), 2.23 (s, 3H), 2.02–1.38 (m, 24H); MS (ESI) m/z 743 (MH+).

EXAMPLE 3

N-[1R-[2-Adamantan-2-yl-oxy)carbonyl]-amino-3-(1H-indol-3-yl)-2S-methyl-propionylamino-methyl]-5-(3-o-tolyl-ureido)-pentyl]-succinamic acid Example 3 was prepared analogously to Example 1. Hence, Intermediate O (182.0 mg, 0.50 mmol) was coupled to Intermediate G (200.0 mg, 0.50 mmol) to give the product (64.8 mg, 17%) after preparative RP-HPLC purification (60–90% B in A, 30 min). The lyophile was >98% pure as determined on analytical RP-HPLC: tr=29.73 (60–90% B, 30 min). $R_f$ (10:1:0.1, methylene chloride:methanol:acetic acid)=0.27; $^1$HNMR (300 MHz, CD$_3$OD) d 7.50 (d, J=8.0 Hz, 2H), 7.31 (d, J=8.0 Hz, 1H), 7.20–6.90 (m, 6H), 3.88 (s, 1H), 3.38 (m, 2H), 3.19–3.0 (m, 4H), 2.58 (m, 24H); MS (ESI) m/z 743 (MH+).

EXAMPLE 4

N-[1R-[2S-Adamantan-2-yl-oxy)carbonyl]-amino-3-(1H-indol-3-yl)propionylamino-methyl]-5-(3-o-tolyl-ureido)-pentyl]-succinamic acid Example 4 was prepared analogously to Example 1. Hence, Intermediate O (100 mg, 0.27 mmol) was coupled to Intermediate J (105 mg, 0.27 mmol) to give the product (92.7 mg, 0.127 mmol, 46%) after RP-HPLC purification (60–80% B-30 min). The lyophile was >98% pure as determined on analytical RP-HPLC: tr=21.60 (60–80% B in A, 30 min). $^1$HNMR (300 MHz, CD$_3$OD) d 7.52 (d, J=7.6 Hz, 1H), 7.41(d, J=7.8 Hz, 1H), 7.24 (d, J=7.8 Hz, 1H), 6.88–7.08(m, 6H), 4.59 (b, 1H), 4.30–4.32 (m, 1H), 3.76 (s, 1H), 2.94–3.18 (m, 6H), 2.46–2.48 (s, 2H), 2.24–2.32 (m, 2H), 2.14 (s, 3H), 1.08–2.01 (m, 20H); MS (ESI) m/z 729 (MH+).

EXAMPLE 5

N-[1R-[2R-Adamantan-2-yl-oxy)carbonyl]-amino-3-(1H-indol-3-yl)propionylamino-methyl]-5-(3-o-tolyl-ureido)-pentyl]-succinamic acid Example 5 was prepared analogously to Example 1. Hence, Intermediate O (100 mg, 0.274 mmol) was coupled to Intermediate H (105 mg, 0.274 mmol) to give the product (75.8 mg, 0.104 mmol, 38%) after RP-HPLC purification (60–80% B in A, 30 min). The lyophile was >98% pure as determined on analytical RP-HPLC: tr=20.1 (60–80% B in A, 30 min). $^1$HNMR (300 MHz, CD$_3$OD) d 7.51 (d, J=7.6 Hz, 1H), 7.42(d, J=7.8 Hz, 1H), 7.23 (d, J=7.8 Hz, 1H), 6.91–7.08(m, 6H), 4.59–4.65(m, 1H), 4.30–4.32 (m, 1H), 3.72–3.73 (m, 1H), 3.00–3.16 (m, 6H), 2.47–2.49 (m, 2H), 2.31–3.34 (m, 2H), 2.15 (s, 3H), 1.27–1.97 (m, 20H); MS (ESI) m/z 729 (MH+).

EXAMPLE 6

N-[1S-[2-Adamantan-2-yl-oxy)carbonyl]-amino-3-(1H-indol-3-yl)-2RS-methyl-propionylamino-methyl]-5-(3-o-tolyl-ureido)-pentyl]-succinamic acid Step 1

A solution of Intermediate E (100 mg, 0.252 mmol), EDC (490 mg, 0.252 mmol) Intermediate S (100 mg, 0.252 mmol) and HOBT (34.0 mg, 0.252 mmol) in methylene chloride (5 mL) was stirred at room temperature for 16 h. The solvent was removed in vacuo and the residue dissolved in ethyl acetate (10 mL). The organic layer was washed with 2N aqueous hydrochloric acid (10 mL), 2N sodium hydroxide solution (10 mL) and brine (10 mL), dried (MgSO$_4$) and concentrated in vacuo to afford the product (145 mg) as a colorless foam which was used crude in the following reaction. $R_f$ (9:1:0.1, CH$_2$Cl$_2$:MeOH:NEt$_3$)=0.52; MS (ESI) m/z 777.4 (MH+).

Step 2

A mixture of the coupled product from Step 1 (147 mg, 0.189 mmol) and 10% palladium on carbon (20 mg) in 1:1 methanol: acetic acid (6 mL) was shaken under hydrogen at 50 psi. After 3 h the solids were removed by filtration through celite and the filtrate concentrate in vacuo to afford the compound as a tan solid (111 mg) which was used crude in the next step. $R_f$(9:1:0.1, methylene chloride:methanol:triethylamine)=0.26; $^1$HNMR (300 MHz, CD$_3$OD) d, 7.36 (t, 2H), 7.20 (d, 1H), 6.8–7.01 (m, 9H), 3.03–3.28 (m, 5H), 2.12 (s, 3H), 1.34–1.91 (m, 24H); MS (ESI) m/z 643.4 (MH+).

Step 3

Triethylamine (48 mL) was added to a solution of the above intermediate (111 mg, 0.172 mmol) in methylene chloride (2 mL) followed by succinic anhydride (18.11 mg, 0.181 mmol) and the resultant solution stirred at room temperature for 16 h. The solvents were removed in vacuo and the residue purified by flash column chromatography (9:1:0.1, methylene chloride:methanol:acetic acid) as the eluant. The product was purified by preparative RP-HPLC (80–100% B in A, 30 min) to give 27.3 mg as a fluffy pink lyophile. The lyophile was >98% pure as determined on analytical RP-HPLC: tr=17.73 and 18.22 (80–100% B in A, 30 min). $R_f$ (9:1:0.1, methylene chloride:methanol:acetic acid)=0.33; MS (ESI) m/z 743.4 (MH+)

EXAMPLE 7

N-[1S-[2-Adamantan-2-yl-oxy)carbonyl]-amino-3-(1H-indol-3-yl-2S-methyl-propionylamino-methl]-5-(3-o-tolyl-ureido)pentyl]-succinamic acid This was prepared analogously to Example 6. Hence Intermediate S (200 mg, 0.504 mmol) and Intermediate G (200 mg, 0.504 mmol) gave the product (47.6 mg) as a white lyophile after purification by preparative RP-HPLC (60–90% B in A, 30 min). The lyophile was >98% pure as determined on analytical RP-HPLC: tr=23.83 min (60–90% B in A, 30 mins); $^1$HNMR (300 MHz, CDCl$_3$) d 8.42 (b, 1H), 7.6 (d, 1H), 7.0–7.4 (m, 11H), 6.82 (t, 1H), 5.41 (b, 1H), 4.82 (b, 1H), 3.60 (b, 1H), 3.2 (b, 2H), 2.62 (b, 2H), 2.38 (b, 2H), 2.22 (s, 3H), 1.2–2.0 (m, 24H); MS (ESI) m/z 743.4 (MH+).

EXAMPLE 8

N-[1S-[2-Adamantan-2-yl-oxy)carbonyl]-amino-3-(1H-indol-3-yl)-2R-methyl-propionylamino-methyl]-5-(3-o-tolyl-ureido)-pentyl]-succinamic acid This was prepared analogously to Example 6. Hence Intermediate S (200 mg, 0.504 mmol) and Intermediate F (200 mg, 0.504 mmol) gave the product (35.2 mg) as a white lyophile after purification by preparative RP-HPLC (60–90% B in A, 30 min). The material was >98% pure, as determined on analytical RP-HPLC: tr=22.64 min (60–90% B in A, 30 min); $^1$HNMR (300 MHz, CDCl$_3$) d 8.50 (b, 1H), 7.57 (d, 1H), 6.85–7.4 (m, 10H), 5.46 (b, 1H), 4.8 (b, 1H), 3.8 (b, 1H), 3.2 (b, 2H), 2.6 (b, 2H), 2.38 (b, 2H), 2.23 (s, 3H), 1.4–2.0 (m, 24H); MS (ESI) m/z 743.4 (MH+).

EXAMPLE 9

N-[1S-[2S-Adamantan-2-yl-oxy)carbonyl]-amino-3-(1H-indol-3-yl)propionylamino-methyl]-5-(3-o-tolyl-ureido)-pentyl]-succinamic acid

Step 1

This was prepared in a similar manner to Example 6. Hence intermediate S (78.0 mg, 0.196 mmol) and intermediate J (75.0 mg, 0.196 mmol) gave the product (107.4 mg) as a tan solid which was used crude in the next reaction. R$_f$ (9:1:0.1, CH$_2$Cl$_2$:MeOH:NEt$_3$)=0.57; MS (ESI) m/z 763.4 (MH+).

Step 2

This was prepared in a similar manner to step 2 of Example 6. Hence the material from step 1 (106.0 mg, 0.138 mmol) gave the product (97 mg) as a tan solid which was used crude in the next reaction; R$_f$(9:1:0.1, methylene chloride:methanol:triethylamine) =0.25.

Step 3

This was prepared in a similar manner to Example 6. Hence the material from step 2 (117 mg, 0.169 mmol) gave the product (19.8 mg) as a white lyophile. This was >98% pure on RP-HPLC: (80–100% B in A, 30 min); R$_f$ (9:1:0.1, methylene chloride:methanol:triethylamine)=0.35; $^1$HNMR (300 MHz, CDCl$_3$), d 8.35 (b, 1H), 7.54 (b, 1H), 7.10–7.35 (m, 9H), 6.86 (t, 1H), 5.4 (b, 1H), 4.82 (b, 1H), 3.52 (b, 1H), 3.22 (b, 2H), 2.59 (b, 2H), 2.62 (b, 2H), 2.43 (b, 2H), 2.22 (b, 3H), 1.2–2.0 (m, 22H); MS (ESI) m/z 79.2 (MH+).

EXAMPLE 10

N-[1S-[2R-Adamantan-2-yl-oxy)carbonyl]-amino-3-(1H-indol-3-yl)propionylamino-methyl]-5-(3-o-tolyl-ureido)-pentyl]-succinamic acid

Step 1

This was prepared in a similar manner to Example 6. Hence, Intermediate S (78.0 mg, 0.196 mmol) and Intermediate H (75.0 mg, 0.196 mmol) gave the product (138 mg) as a colorless foam which was used crude in the following reaction; R$_f$ (9:1:0.1; CH$_2$Cl$_2$:MeOH:-NEt$_3$)=0.56; MS (ESI) m/z 763.2 (MH+).

Step 2

This was prepared in a similar manner to step 2 of Example 6. Hence the material from step 1 (135 mg, 0.177 mmol) gave the product (89.9 mg) as a tan solid which was used crude in the next reaction; R$_f$(9:1:0.1, CH$_2$Cl$_2$:MeOH:Et$_3$N)=0.25; MS (ESI) m/z 629.4 (MH+).

Step 3

This was prepared in a similar manner to Example 6. Hence the material from step 2 (88.0 mg, 0.127 mmol) gave the product (21.8 mg) as a white lyophile, which was >98% pure on RP-HPLC: tr=5.32 min (80–100% B in A, 30 min). R$_f$ (9:1:0.1, methylene chloride:methanol:acetic acid)=0.35; $^1$HNMR (300 MHz, CDCl$_3$), d 8.4 (b, 1H), 7.59 (d, 1H), 7.0–7.40 (m, 11H), 6.83 (t, 1H), 5.4 (b, 1H), 4.82 (b, 1H), 3.6 (b, 1H), 3.2 (b, 2H), 2.62 (b, 2H), 2.4 (b, 2H), 2.25 (s, 3H), 1.2–2.0 (m, 20H); MS (ESI) m/z 729.2 (MH+).

EXAMPLE 11

N-[1R-[2-Adamantan-2-yl-oxy)carbonyl]-amino-3-(1H-indol-3-yl)-2RS-methyl-propionylamino-methyl]-4-(3-o-tolyl-ureido)-butyl]-succinamic acid This was prepared in a analogous manner to Example 6. Hence Intermediate U (100 mg, 0.262 mmol) and Intermediate E (103 mg, 0.262 mmol) gave the product (103.0 mg) as a white lyophile after purification by RP-HPLC (60–90% B in A, 30 min); The lyophile was >98% pure as determined on analytical RP-HPLC: tr=22.95 min (60–90% B in A, 30 min); MS (ESI) m/z 729.4 (MH+).

EXAMPLE 12

N-[1S-[2-Adamantan-2-yl-oxy)carbonyl]-amino-3-(1H-indol-3-yl)-2RS-methyl-propionylamino-methyl]-4-(3-o-tolyl-ureido)-butyl]-succinamic acid

Step 1

This was prepared in a similar manner to Example 6. Hence Intermediate W (80.0 mg, 0.228 mmol) and Intermediate E (90.7 mg, 0.228 mmol) gave the product (142 mg) as a white powder which was used crude in the next reaction. R$_f$(9:1:0.1; CH$_2$Cl$_2$:MeOH:NEt$_3$)=0.51; MS (ESI) m/z 729 (MH$_+$).

Step 2

The material from step 1 (140 mg, 0.192 mmol) was stirred in 4N hydrogen chloride in dioxane (2 mL) at room temperature for 2 h. Ether (10 mL) was added and the resultant solid isolated by filtration to afford the product (84 mg) as a white solid which was used crude for the next reaction. R$_f$(9:1:0.1, methylene chloride:-methanol:triethylamine)=0.28; MS (ESI) m/z 629.4 (MH+).

Step 3

This was prepared in a similar manner to Example 6. Hence the material from step 2 (84.0 mg, 0.126 mmol) gave the crude product. The product was purified by preparative RP-HPLC (75-100% B in A, 30 minutes) and isolated as a white lyophile. Analytical RP-HPLC showed an equal mixture of diastereomers, tr=11.46 and 11.78 min (75-100% B in A, 30 min); $R_f$ (9:1:0.1, methylene chloride:methanol:acetic acid)=0.32; MS (ESI) m/z 729.2 (MH+);

EXAMPLE 13

N-[1R-[2R-Adamantan-2-yl-oxy)carbonyl]-amino-3-(1H-indol-3-yl)propionylamino-methyl]-4-(3-o-tolyl-ureido)-butyl]-succinamic acid Step 1

This was prepared in a similar manner to Example 6. Hence Intermediate U (100 mg, 0.262 mmol) and Intermediate H (100 mg, 0.262 mmol) gave the product (180 mg) as a clear glass. This was used crude in the next reaction. $R_f$ (9:1:0.1; CH$_2$Cl$_2$:MeOH:NEt$_3$)=0.55; MS (ESI) m/z 749.4 (MH+).

Step 2

This was prepared in a similar manner to step 2 from Example 6. Hence the material from step 1 (180 mg, 0.240 mmol) gave the product (142 mg) as a tan solid which was used crude in next reaction. MS (ESI) m/z 615.1 (MH+).

Step 3

This was prepared in a similar manner to Example 6. Hence the material from step 2 (142 mg, 0.235 mmol) gave the product (50.5 mg) as a pale pink lyophile after purification by preparative RP-HPLC (60-90% B in A, 30 min). The material was >98% pure as determined on analytical RP-HPLC: tr=23.72 min (60-90% B in A, 30 min), $^1$HNMR (300 MHz, CDCl$_3$), d 9.20 (b, 1H), 7.61 (b, 1H), 7.0-7.40 (m, 9H), 6.92 (t, 1H), 5.4 (b, 1H), 4.80 (b, 1H), 3.49 (b, 1H), 2.9-3.2 (b, 4H), 2.61 (b, 2H), 2.20 (s, 3H), 1.2-20 (m, 18H); MS (ESI) m/z 715.4 (MH+).

EXAMPLE 14

N-[1R-[2S-Adamantan-2-yl-oxy)carbonyl]-amino-3-(1H-indol-3-yl)propionylamino-methyl]-4-(3-o-tolyl-ureido)-butyl]-succinamic acid Step 1

This was prepared in a similar manner to step 1 of Example 9. Hence Intermediate U (100 mg, 0.262 mmol) and Intermediate J (100 mg, 0.262 mmol) gave the product as a colorless glass (161 mg) which was also used crude in following reaction. $R_f$ (9:1:0.1; CH$_2$Cl$_2$:MeOH:NEt$_3$)=0.55; MS (ESI) m/z 749.4 (MH+).

Step 2

This was prepared in an analogous manner to Example 6. Hence the material from step 1 (161 mg, 0.21 5 mmol) gave the product (49.3 mg) as a white lyophile after purification by preparative RP-HPLC (60-90% B in A, 30 mins). The material was >98% pure as determined on analytical RP-HPLC: tr=22.87 min (60-90% B in A, 30 mins), $^1$HNMR (300 MHz, CDCl$_3$) d 8.78 (b, 1H), 7.62 (d, 1H), 7.1-7.45 (m, 9H), 6.75 (b, 1H), 5.69 (b, 1H), 4.80 (s, 1H), 4.56 (b, 1H), 3.1-3.6 (water peak), 2.60 (b, 2H), 2.25 (s, 3H), 1.05-1.95 (m, 18H); MS (ESI) m/z 715.4 (MH+).

EXAMPLE 15

N-[1S-[2S-Adamantan-2-yl-oxy)carbonyl]-amino-3-(1 H-indol-3-yl)propionylamino-methyl]-4-(3-o-tolyl-ureido)-butyl]-succinamic acid This was prepared in a similar manner to Example 6. Hence Intermediate V (150 mg, 0.392 mmol) and Intermediate J (150 mg, 0.392 mmol) gave the product (46.0 mg) as a white lyophile after purification by preparative RP-HPLC (60-90% B in A, 30 min). The material was >98% pure as determined on analytical RP-HPLC: tr=21.96 min (60-90% B in A, 30 min). $^1$HNMR (300 MHz, CDCl$_3$) d 9.38 (b, 1H), 7.54 (d, 1H), 6.9-7.4 (m, 9H), 6.86 (b, 1H), 5.70 (b, 1H), 4.48 (b, 1H), 3.60 (b, 2H), 3.16 (b, 2H), 2.6 (b, 2H), 2.26 (s, 3H), 1.05-1.95(m, 18H); MS (ESI) m/z 715.4 (MH+).

EXAMPLE 16

N-[1S-[2R-Adamantan-2-yl-oxy)carbonyl]-amino-3-(1H-indol-3-yl)propionylamino-methyl]-4-(3-o-tolyl-ureido)-butyl]-succinamic acid This was prepared in a similar manner to Example 6. Hence Intermediate V (150 mg, 0.392 mmol) and Intermediate H (150 mg, 0.392 mmol) gave the product (134 mg) as a white lyophile after purification by preparative RP-HPLC (60-90% B in A, 30 min). The material was >98% pure on analytical RP-HPLC: tr=20.46 min (60-90% B in A, 30 min). $^1$HNMR (300 MHz, CDCl$_3$) d 8.98 (b, 1H), 7.70 (m, 1H), 6.9-7.5 (m, 9H), 6.90 (b, 1H), 5.62 (b, 1H), 4.52 (b, 1H), 3.60 (b, 1H), 2.8-3.5 (H$_2$O peak), 2.50 (b, 2H), 2.22 (s, 3H), 1.02-1.95 (m, 18H); MS (ESI) m/z 715.4 (MH+).

EXAMPLE 17

N-[1R-[1-(Adamantan-2-yl-oxy)carbamoyl)-2-(1H-indol-3-yl)-1RS-methyl-ethyl-carbamoylmethyl]-5-(3-o-tolyl-ureido)-pentyl]-succinamic acid Step 1

To a solution of Intermediate N (0.169 g, 0.43 mmol), and Intermediate R (0.176 g, 0.43 mmol), N-hydroxybenzotriazole (0.058 g, 0.43 mmol) in N,N-dimethylformamide (5 mL) was added BOP reagent (0.19 g, 0.43 mmol). The reaction mixture was stirred overnight. The DMF was removed in vacuo and the residue was partitioned between ethyl acetate (20 mL) and 1N aqueous NaOH (20 mL). The organic layer was separated and washed successively with water (20 mL), 10% aqueous citric acid (20 mL), and water (5 mL), dried over sodium sulfate and evaporated in vacuo to an amorphous solid (0.273 g, 0.37 mmol) which was used without further purification. $R_f$ (250:25:1, methylene chloride methanol:acetic acid)=0.39; MS (FAB) m/z 727 (MH+)

Step 2

The product from the previous step (200 mg, 0.28 mmol) was dissolved in 4N HCl in 1,4-dioxane (10 mL) and 0.2 mL anisole and stirred at 0° C. for 2 h. The 1,4-dioxane was evaporated and the residual oil was triturated with ethyl acetate to afford the amine hydrochloride salt as an amorphous pink solid (157 mg, 0.25 mmol); MS (FAB) m/e 627 (MH+).

Step 3

The product from the previous step (155 mg, 0.25 mmol) was suspended in ethyl acetate (10 mL) and triethylamine (0.048 mL, 0.25 mmol) and succinic anhydride (0.023 g, 0.25 mmol) was added. The mixture was sonicated 15 minutes, then allowed to stir at room temperature overnight. The reaction mixture was diluted with ethyl acetate (20 mL), washed with 10% aqueous citric acid (20 mL), water (20 mL), dried (Na2SO4) and concentrated in vacuo to give an amorphous solid. Example 17 was purified by preparative RP-HPLC: tr=24.0 min (60%–90% B in A, 30 min). On analytical RP-HPLC the diastereomers overlapped at tr=16.5 min (30–60% B in A); MS FAB m/e 727 (MH+).

EXAMPLE 18

N-[1R-[2-[(Benzyloxy)carbonyl]-amino-3-(1H-indol-3-yl)-2RS-methyl-propionylamino-methyl]-5-(3-o-tolyl-ureido)-pentyl]-succinamic acid Step 1

The product was obtained from the coupling of Intermediate K (0.352 g, 0.0013 mol) and Intermediate O (0.49 g, 0.0013 mol) using EDC/HOBt as previously described. The crude material (0.917 g) was used in the next step without further purification. $R_f$ (9:1, methylene chloride:methanol)=0.44; MS (FAB) m/e 699 (MH+).

Step 2

The product from the previous step was dissolved in 4N HCl dioxane (10 mL) and anisole (0.2 mL) and stirred for two hours at 0° C. The dioxane was evaporated in vacuo and the residue was triturated with ether to give the product as a white amorphous solid (723 mg). $R_f$ (9:1, methylene chloride:methanol)=0.09; MS(FAB) m/e 599 (MH+).

Step 3

The product from the previous step (0.723 g, 1.20 mmol) was suspended in ethyl acetate (50 mL) and triethylamine (0.167 mL) and succinic anhydride (0.114 g, 0.0012 mol) were added. The mixture was sonicated for 30 minutes, then allowed to stir overnight. The reaction mixture was diluted with ethyl acetate (50 mL) and washed with 10% aqueous citric acid and water. The organic layer was dried (Na2SO4) and concentrated in vacuo to give 0.712 g of crude product. $R_f$ (250:24:1, methylene chloride:methanol:acetic acid)=0.31. A portion of this material (147 mg) was purified by preparative RP-HPLC (50–80% B in A, 30 min). The product was collected and lyophilized to an amorphous white solid. On analytical RP-HPLC, the product diastereomers elute as a broad single peak: tr=19.8 min (50–80 % B in A, 30 min). MS (FAB) m/e 699 (MH+).

Intermediate Example i

N-[1R-[2-Amino-3-(1H-indol-3-yl)-2RS-methyl-propionylamino-methyl]-5-(3-o-tolyl-ureido)-pentyl]-succinamic acid To a portion of Example 18 (350 mg) dissolved in glacial acetic acid (10 mL) and methanol (5 mL) was added 10% palladium on carbon (50 mg). This mixture was shaken under a 50 psi H2 atmosphere overnight, then filtered through a celite pad. The celite pad was washed with methanol (100 mL) and the filtrate was concentrated in vacuo. A portion of this material was purified by preparative RP-HPLC (40%–70% B in A, 30 min). The product was collected and lyophilized to an amorphous white solid. A slight separation of diastereomers could be observed on analytical RP-HPLC: tr=7.8 min and 8.0 min (40–70% B in A, 30 min). $R_f$(250:25:1, methylene chloride:methanol:acetic acid)=0.02; MS (FAB) m/e 565 (MH+).

EXAMPLE 19

N-[1R-[2-Acetylamino-3-(1H-indol-3-yl)-2RS-methyl-propionylamino-methyl]-5-(3-o-tolyl-ureido)-pentyl]-succinamic acid A portion of the product of Intermediate Example i (0.05 g) was dissolved in a solution of DMF (1 mL), pyridine (1 mL) and acetic anhydride (1 mL) and stirred for 15 minutes at room temperature. The solvent was concentrated in vacuo and the material purified by preparative RP-HPLC (40–70% B in A, 30 min). The product was collected and lyophilized to an amorphous white solid. No separation of diastereomers was observed on analytical RP-HPLC: tr=15 min (40–70% B in A, 30 min). MS (FAB) m/e 591 (MH+).

We claim:

1. A compound which has the following Formula Ia:

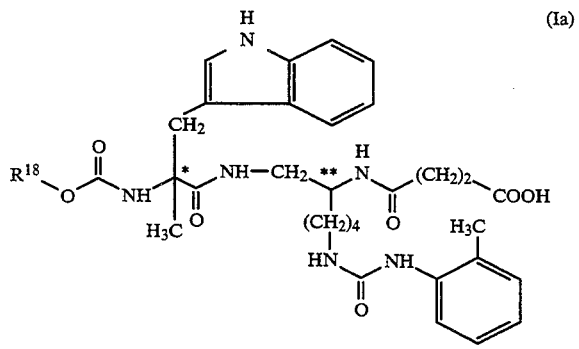

wherein $R^{18}$ is benzyl, adamantyl, t-butyl or trans-2-methylcyclohexyl.

2. A compound which has the following Formula (Ib):

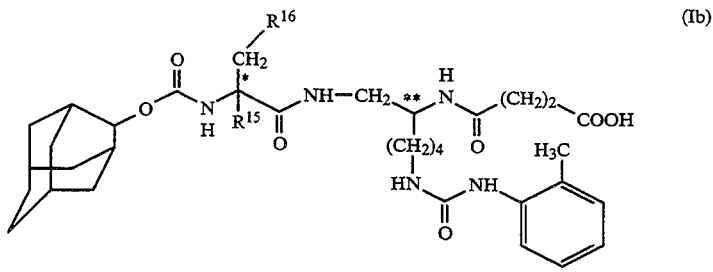

wherein $R^{15}$ is methyl or hydrogen and $R^{16}$ is 3-indolyl or 2-indolyl.

3. A compound which has the following formula (Ic):

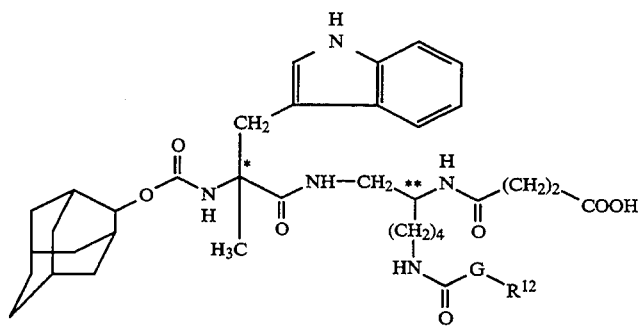

(Ic)

wherein G is —O— or —NH— and $R^{12}$ is phenyl, 2-methylphenyl, 2-chlorophenyl, 2-methoxyphenyl or 2-nitrophenyl; or G is —CH=CH— and $R^{12}$ is phenyl, 4-methylphenyl, 4-chlorophenyl, 4-methoxyphenyl, 4-hydroxyphenyl or 4-nitrophenyl; or G is —CH$_2$— or —CH$_2$CH$_2$— and $R^{12}$ is any of the values as defined herein above for $R^{12}$.

4. A compound which has the following formula (Id):

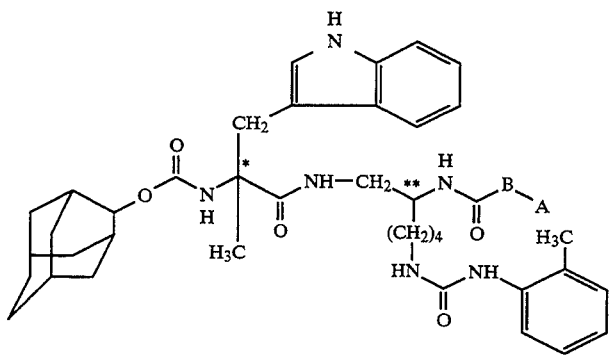

(Id)

wherein B is —CH=CH— or (CH$_2$)$_n$, wherein n=1, 2 or 3 and A is CO$_2$H, CO$_2$CH$_3$, 5-tetrazolyl, NHSO$_2$CF$_3$ or NHSO$_2$CH$_3$.

5. A compound which has the following formula (Ie):

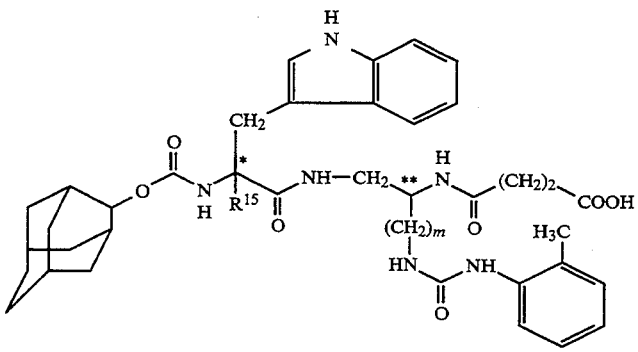

(Ie)

wherein $R^{15}$ is CH$_3$; m is 3 or 4; or wherein $R^{15}$ is H; m is 1-4.

6. A compound selected from the group consisting of the following compounds:

N-[1R-[2-adamantan-2-yl-oxy)carbonyl]-amino-3-(1H-indol-3-yl)-2RS-methyl-propionylamino-methyl]-5-(3-o-tolyl-ureido)-pentyl]-succinamic acid, N-[1R-[2-adamantan-2-yl-oxy)carbonyl]-amino-3-(1H-indol-3-yl)-2R-methyl-propionylamino-methyl]-5-(3-o-tolyl-ureido)-pentyl]-succinamic acid, N-[1R-[2-adamantan-2-yl-oxy)carbonyl]-amino-3-(1H-indol-3-yl)-2S-methyl-propionylamino-methyl]-5-(3-o-tolyl-ureido)-pentyl]-succinamic acid, N-[1R-[2S-[2-adamantan-2-yl-oxy)carbonyl]-amino-3-(1H-indol-3-yl)propionylamino-methyl]-5-(3-o-tolyl-ureido)-pentyl]-succinamic acid, N-[1R-[2R-[2-adamantan-2-yl-oxy)carbonyl]-amino-3-(1H-indol-3-yl)propionylamino-methyl]-5-(3-o-tolyl-ureido)-pentyl]-succinamic acid, N-[1S-[2-adamantan-2-yl-oxy)carbonyl]-amino-3-(1H-indol-3-yl)-2RS-methyl-propionylamino-methyl]-5-(3-o-tolyl-ureido)-pentyl]-succinamic acid, N-[1S-[2-adamantan-2-yl-oxy)carbonyl]-amino-3-(1H-indol-3-yl)-2S-methyl-propionylamino-methyl]-5-(3-o-tolyl-ureido)-pentyl]-succinamic acid, N-[1S-[2-adamantan-2-yl-oxy)carbonyl]-amino-3-(1H-indol-3-yl)-2R-methyl-propionylamino-methyl]-5-(3-o-tolyl-ureido)-pentyl]-succinamic acid, N-[1S-[2S-adamantan-2-yl-oxy)carbonyl]-amino-3-(1H-indol-3-yl)propionylamino-methyl]-5-(3-o-tolyl-ureido)-pentyl]-succinamic acid, N-[1S-[2R-adamantan-2-yl-oxy)carbonyl]-amino-3-(1H-indol-3-yl)propionylamino-methyl]-5-(3-o-tolyl-ureido)-pentyl]-succinamic acid, N-[1R-[2-adamantan-2-yl-oxy)carbonyl]-amino-3-(1H-indol-3-yl)-2RS-methyl-propionylamino-methyl]-4-(3-o-tolyl-ureido)-butyl]-succinamic acid, N-[1S-[2-adamantan-2-yl-oxy)carbonyl]-amino-3-(1H-indol-3-yl)-2RS-methyl-propionylamino-methyl]-4-(3-o-tolyl-ureido)-butyl]-succinamic acid, N-[1R-[2R-adamantan-2-yl-oxy)carbonyl]-amino-3-(1H-indol-3-yl)propionylamino-methyl]-4-(3-o-tolyl-ureido)-butyl]-succinamic acid, N-[1R-[2S-adamantan-2-yl-oxy)carbonyl]-amino-3-(1H-indol-3-yl)propionylamino-methyl]-4-(3-o-tolyl-ureido)-butyl]-succinamic acid, N-[1S-[2S-adamantan-2-yl-oxy)carbonyl]-amino-3-(1H-indol-3-yl)propionylamino-methyl]-4-(3-o-tolyl-ureido)-butyl]-succinamic acid, N-[1S-[2R-adamantan-2-yl-oxy)carbonyl]-amino-3-(1H-indol-3-yl)propionylamino-methyl]-4-(3-o-tolyl-ureido)-butyl]-succinamic acid, N-[1R-[1-adamantan-2-yl-oxy)carbonyl]-2-(1H-indol-3-yl)-1RS-methylethyl-carbamoylmethyl]-5-(3-o-tolyl-ureido)-pentyl]-succinamic acid, N-[1R-[2-benzyloxy)carbonyl]-amino-3-(1H-indol-3-yl)-2RS-methyl-propionylamino-methyl]-5-(3-o-tolyl-ureido)-pentyl]-succinamic acid, N-[1R-[2-amino-3-(1H-indol-3-yl)-2RS-methyl-propionylamino-methyl]-5-(3-o-tolyl-ureido)-pentyl]-succinamic acid or N-[1R-[2-acetylamino-3-(1H-indol-3-yl)-2RS-methyl-propionylamino-methyl]-5-(3-o-tolyl-ureido)-pentyl]-succinamic acid.

* * * * *